US010344300B2

(12) United States Patent
Chen et al.

(10) Patent No.: US 10,344,300 B2
(45) Date of Patent: Jul. 9, 2019

(54) NANOTUBES AS CARRIERS OF NUCLEIC ACIDS INTO CELLS

(71) Applicants: Brown University, Providence, RI (US); Rhode Island Hospital, Providence, RI (US)

(72) Inventors: Yunpeng Chen, Mansfield, MA (US); Qian Chen, Barrington, RI (US); Thomas J. Webster, Barrington, RI (US); Hicham Fenniri, Edmonton (CA); Usha Devi Hemraz, Edmonton (CA)

(73) Assignees: Brown University, Providence, RI (US); Rhode Island Hospital, Providence, RI (US); The Governors of the University of Alberta, Edmonton (CA); National Research Council of Canada, Ottawa (CA)

( * ) Notice: Subject to any disclaimer, the term of this patent is extended or adjusted under 35 U.S.C. 154(b) by 0 days.

(21) Appl. No.: 14/662,334

(22) Filed: Mar. 19, 2015

(65) Prior Publication Data

US 2015/0258213 A1    Sep. 17, 2015

Related U.S. Application Data

(63) Continuation of application No. 13/977,138, filed as application No. PCT/US2012/020056 on Jan. 3, 2012.

(60) Provisional application No. 61/429,555, filed on Jan. 4, 2011.

(51) Int. Cl.

| | |
|---|---|
| *C12N 15/87* | (2006.01) |
| *C12N 15/11* | (2006.01) |
| *C12N 15/113* | (2010.01) |
| *C12N 15/115* | (2010.01) |
| *A61K 31/713* | (2006.01) |
| *B82Y 5/00* | (2011.01) |
| *A61K 31/675* | (2006.01) |
| *A61K 9/00* | (2006.01) |
| *A61K 48/00* | (2006.01) |
| *C12Q 1/6841* | (2018.01) |

(52) U.S. Cl.
CPC ............ *C12N 15/87* (2013.01); *A61K 9/0092* (2013.01); *A61K 31/675* (2013.01); *A61K 31/713* (2013.01); *A61K 48/005* (2013.01); *A61K 48/0075* (2013.01); *C12N 15/113* (2013.01); *C12N 15/115* (2013.01); *C12Q 1/6841* (2013.01); *B82Y 5/00* (2013.01); *C12N 2310/12* (2013.01); *C12N 2310/14* (2013.01); *C12N 2310/141* (2013.01); *C12N 2320/30* (2013.01)

(58) Field of Classification Search
None
See application file for complete search history.

(56) References Cited

U.S. PATENT DOCUMENTS

| | | |
|---|---|---|
| 6,696,565 B2 | 2/2004 | Fenniri |
| 7,772,201 B2 | 8/2010 | Mixson |
| 8,795,691 B2 | 8/2014 | Webster et al. |

FOREIGN PATENT DOCUMENTS

| | | |
|---|---|---|
| WO | 1992/19195 A1 | 11/1992 |
| WO | 2011116085 A1 | 9/2011 |

OTHER PUBLICATIONS

Alshamsan A et al.: "Efficiency of 1-14 Cationic Rosette Nanotubes for siRNA Delivery". Mater. Res. Soc. Symp. Proc. vol. 1316, copyright 2011, DOI: 10.1557/opl.2011.435.
Arenz, Christoph et al. RNA interference: from an ancient mechanism to a state of the art therapeutic application? Naturwissenschaften 2003; 90:345-359.
Bernstein, Emily et al. Role for a bidentate ribonuclease in the initiation step of RNA interference. Nature 2001; 409:363-366.
Coburn, Glen A. et al. siRNAs: a new wave of RNA-based therapeutics. J Antimicrob Chemother 2003; 51:753-756.
Database Compendex [Online] 1-14 Engineering Information. Inc .• New York. NY. US; 2011. Alshamsan A et al: "Efficiency of cationic rosette nanotubes for siRNA delivery". XP002733380. Database accession No. E20121714970288 * abstract *.
Extended European Search Report issued from corresponding EP 12732496.0, dated Jan. 12, 2015.
Fenniri, Hicham et al. Helical Rosette Nanotubes: Design, Self-Assembly, and Characterization. J. Am. Chem. Soc. 2001, 123, 3854-3855.
Fine, Eli et al. Enhanced endothelial cell functions on rosette nanotube-coated titanium vascular stents. International Journal of Nanomedicine 2009:4 91-97.
Fire, Andrew et al. Potent and specific genetic interference by double-strandedRNAin Caenorhabditis elegans. Nature 1998; 391:806-811.
Hammond, Scott M. et al. An RNA-directed nuclease mediates post-transcriptional gene silencing in *Drosophila* cells. Nature 2000; 404:293-296.
Hammond, Scott M. et al. Argonaute2, a Link Between Genetic and Biochemical Analyses of RNAi. Science 2001; 293:1146-1150.
Journeay, W Shane et al. Low Inflammatory Activation by Self-Assembling Rosette Nanotubes in Human Calu-3 Pulmonary Epithelial Cells. Small. 2008, 4(6):817-823.
Journeay, W Shane et al. Rosette nanotubes show low acute pulmonary toxicity in vivo. Int. J. Nanomedicine, 2008, 3(3):373-383.
Moralez, Jesus G. et al. Helical Rosette Nanotubes with Tunable Stability and Hierarchy. J. Am. Chem. Soc., 2005, 127, 8307-8309.
Reynolds, Angela et al. Rational siRNA design for RNA interference. Nat Biotechnol 2004; 22:326-330.

(Continued)

*Primary Examiner* — Tracy Vivlemore
(74) *Attorney, Agent, or Firm* — Banner & Witcoff, Ltd.

(57) ABSTRACT

The present invention is directed to transfection complexes of rosette nanotubes and one or more nucleic acids.

14 Claims, 24 Drawing Sheets

(56) References Cited

OTHER PUBLICATIONS

Rocheleau, Christian E. et al. Wnt Signaling and an APC-Related Gene Specify Endoderm in Early C. elegans Embryos. Cell 1997; 90:707-716.

Shvedova, Anna A. et al. Unusual inflammatory and fibrogenic pulmonary responses to single-walled carbon nanotubes in mice. Am. J. Physiol Lung Cell Mol. Physiol. Nov. 2005;289(5):L698-708.

Simeoni, Federica et al. Insight into the mechanism of the peptide-based gene delivery system MPG: implications for delivery of siRNA into mammalian cells Nucleic Acids Res 2003; 31:2717-2724.

Suri S S et al: 11 The role of RGD-tagged 1-14 helical rosette nanotubes in the induction of inflammation and apoptosis in human lung adenocarcinoma cells through the P38 MAPK pathwayn. Biomaterials. Elsevier Science Publishers BV .• Barking. GB. vol. 30. No. 17. Jun. 1, 2009 (Jun. 1, 2009). pp. 3084-3090. XP026933213. ISSN: 0142-9612. DOI: 10.1016/J.Biomaterials.2009.02.014 [retrieved on Feb. 27, 2009].

Zhang, Lijie et al. Arginine-glycine-aspartic acid modified rosette nanotube-hydrogel composites for bone tissue engineering. Biomaterials 2009;30(7):1309-1320.

MRS proceedings Table of Contents for vol. 1316, 2010 MRS Fall Meeting Symposium QQ [retrieved on Apr. 23, 2015]. Retrieved from the internet: <URL: http://journals.cambridge.org/action/displayIssue?jid=OPL&volumeId=1316&iid=8195311 >.

2010 MRS Fall Meeting and Exhibit information page, 2 pages [retrieved on Apr. 23, 2015]. Retrieved from the internet: <URL:http://www.mrs.org/fall201 01>.

Alshamsan, A., et al. "Efficiency of Cationic Rosette Nanotubes for siRNA Delivery." Poster presented on Dec. 1, 2010 at the Fall Meeting of the Materials Research Society.

Hemraz, U.D. "Twin GC-based rosette nanotubes: structure and chirality." (2010) (Ph.D. dissertation, University of Alberta).

Symposium QQ: Nanofunctional Materials, Nanostructures, and Nanodevices for Biomedical Applications II; Proceedings of the Materials Research Society Symposium Proceedings Series, Nov. 29-Dec. 3, 2010; Boston, MA; pp. 1-93.

Yang, L., et al., "Nanotechnology controlled drug delivery for treating bone diseases", 2009, Exper. Opin. Drug Deliv., pp. 851-864.

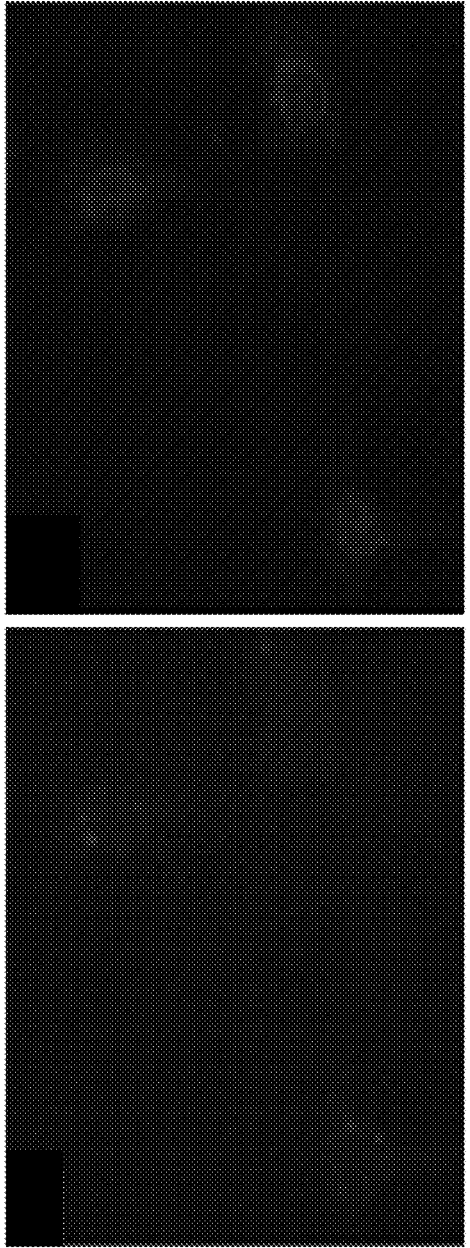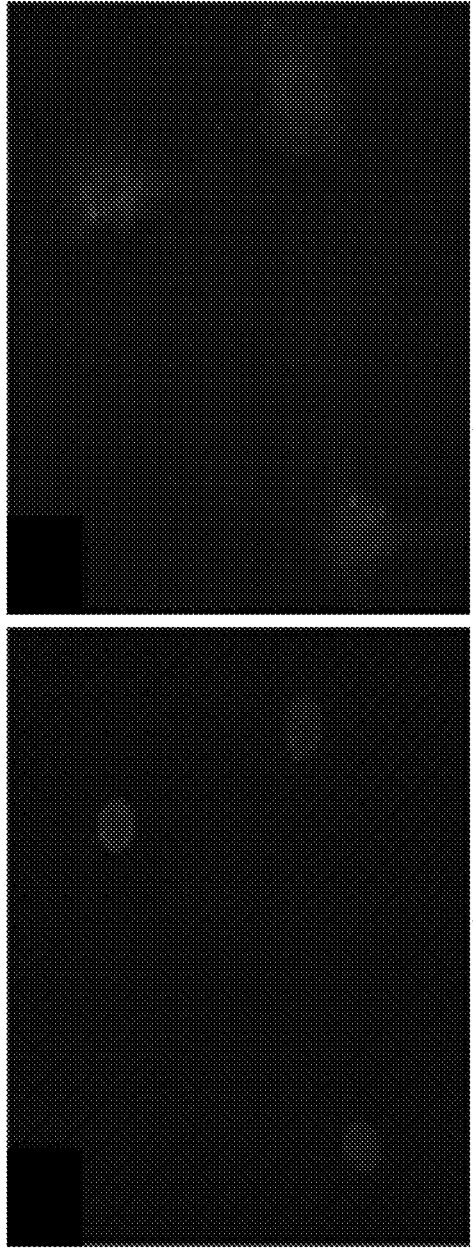

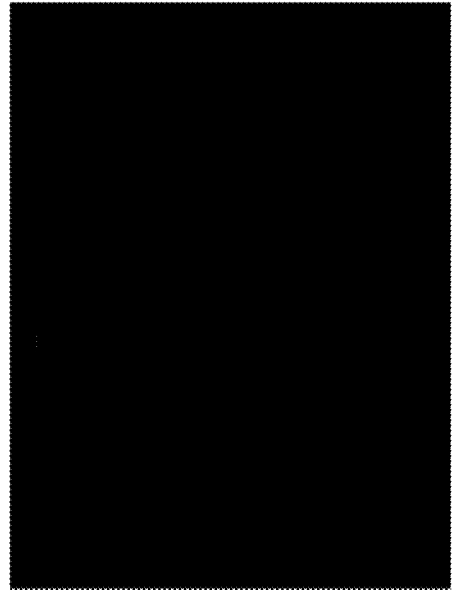
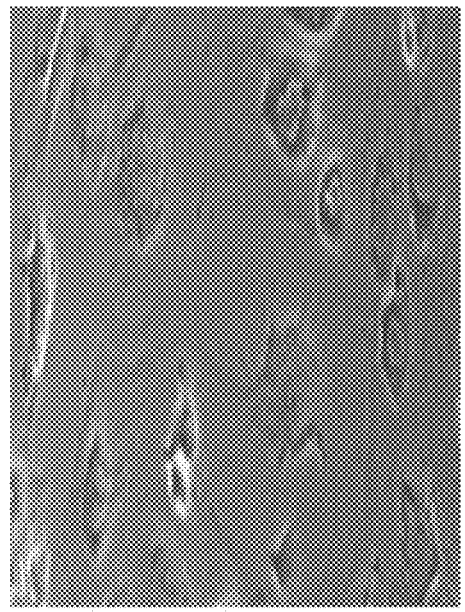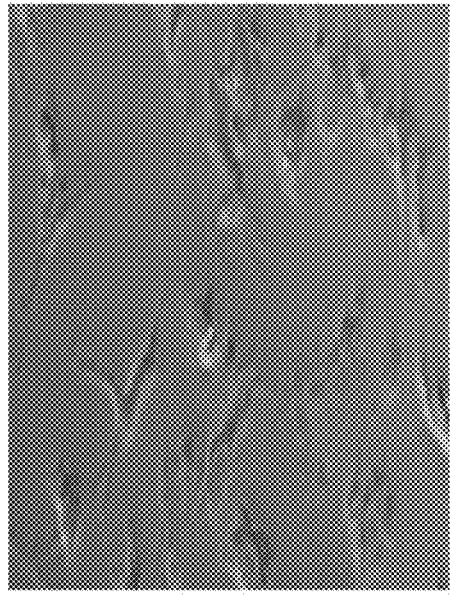

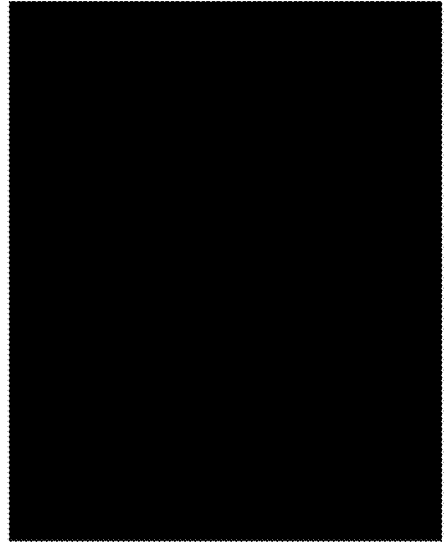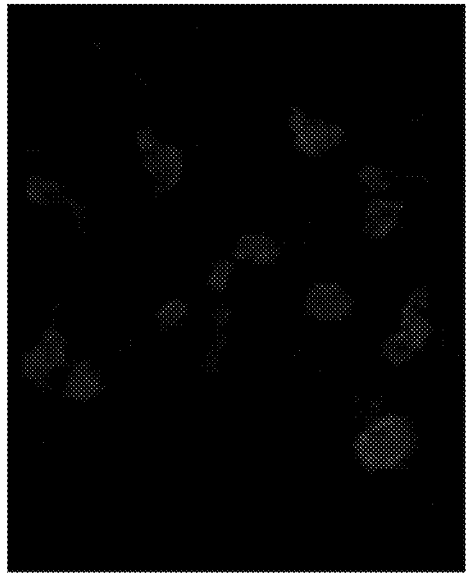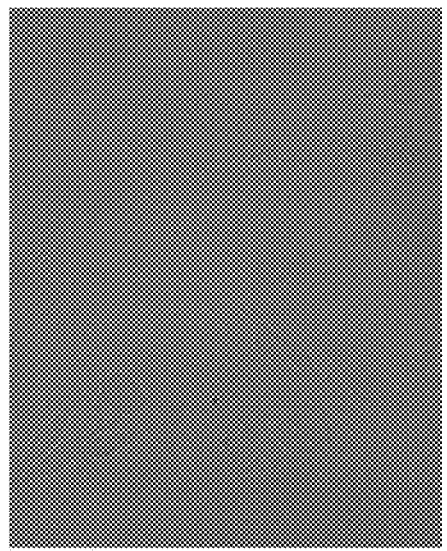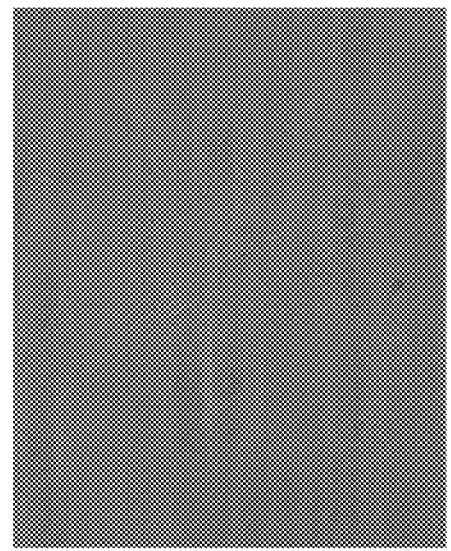

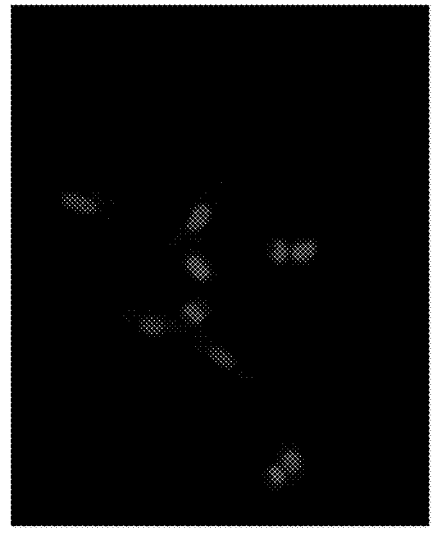
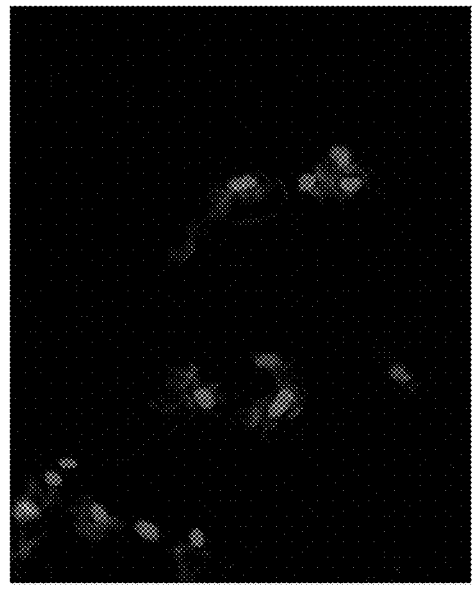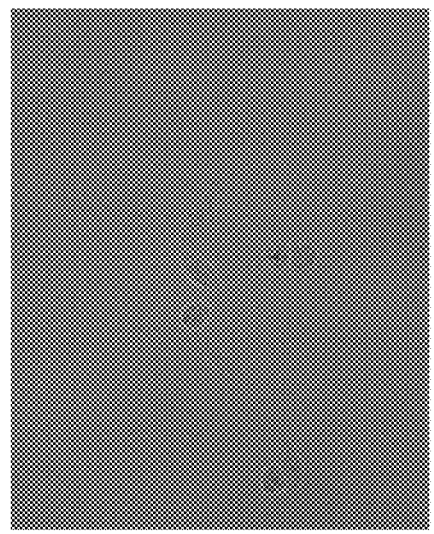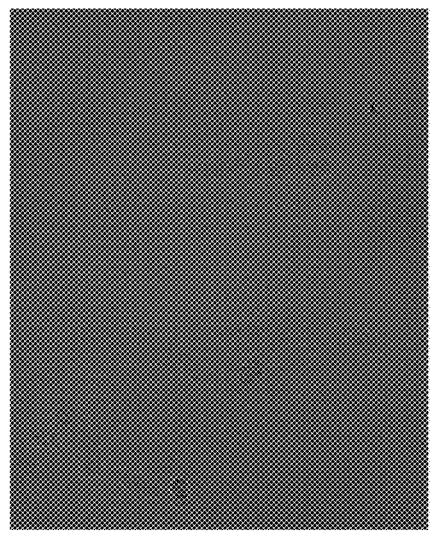

NANOTUBES AS CARRIERS OF NUCLEIC ACIDS INTO CELLS

RELATED APPLICATION DATA

This application is a continuation of U.S. application Ser. No. 13/977,138 filed Jun. 28, 2013 which is a National Stage Application under 35 U.S.C. 371 of co-pending PCT application PCT/US2012/020056 designating the United States and filed Jan. 3, 2012; which claims the benefit of U.S. provisional application No. 61/429,555 and filed Jan. 4, 2011 each of which are hereby incorporated by reference in their entireties.

STATEMENT OF GOVERNMENT INTERESTS

This invention was made with government support under National Institutes of Health grant number P20 RR024484 and R21 AG027521. The Government has certain rights in the invention.

FIELD

Embodiments of the present disclosure relate to the use of rosette nanotubes to deliver nucleic acids into cells. Embodiments of the present disclosure still further relate to complexes of rosette nanotubes and nucleic acids and compositions thereof and the use of such complexes to deliver nucleic acids into the cells of individuals for therapeutic purposes. Embodiments of the present disclosure further relate to the use of rosette nanotubes to deliver interference RNA into cells. Embodiments of the present disclosure further relate to methods of inhibiting target RNA within a cell using complexes of rosette nanotubes and small RNA. Embodiments of the present disclosure still further relate to transfection complexes of rosette nanotubes and nucleic acids such as DNA and RNA and compositions thereof and the use of such transfection complexes to introduce the DNA or RNA into cells, for example as a therapeutic treatment.

BACKGROUND

RNA interference (RNAi) is a system in living cells that helps control genes activity. Mediators of RNAi include two classes of small RNA including microRNA (miRNA) and small interfering RNA (siRNA). Interference RNA molecules have been used to silence genes and consequently their gene products and more efficiently than antisense RNA alone. See Rocheleau C E, et al., *Cell* 1997; 90:707-716.) Interference RNA molecules have been used to study the role of proteins in signal transduction pathways and it has also been suggested that these molecules might be useful in treating a variety of diseases in which the causative protein is overexpressed. See Arenz et al., *Naturwissenschaften* 2003; 90:345-359; Coburn et al., *J Antimicrob Chemother* 2003; 51:753-756. To avoid nonspecific gene silencing induced by longer double-stranded RNA, small interfering RNAs, a duplex of 21-23 nucleotides, have been used as mediators to degrade target mRNA. See Fire et al., *Nature* 1998; 391:806-811.) Once inside the cell, siRNA is incorporated into an RNA-induced silence complex (RISC), a protein-RNA complex that results in unwinding and strand separation of the RNA duplex. The antisense RNA then guides the activated RISC to anneal and cleave the target mRNA. See Hammond et al., *Nature* 2000; 404:293-296; Reynolds et al., *Nat Biotechnol* 2004; 22:326-330; Hammond et al., *Science* 2001; 293:1146-1150; and Bernstein et al., *Nature* 2001; 409:363-366.

Both viral and nonviral carriers have been used to carry interference RNA to their cytosolic mRNA target. See Simeoni et al., *Nucleic Acids Res* 2003; 31:2717-2724. Highly branched HK peptides have also been suggested as carriers of siRNA to transfect eukaryotic cells. See U.S. Pat. No. 7,772,201.

The lipophilic nature of biological membranes restricts direct intracellular delivery of potential drugs or molecular probes. There is a need in the art for transfection complexes having transfection efficiencies sufficient to deliver small RNA into the interior of cells, such as therapeutically effective amounts of siRNA into target cells. There is also a need in the art for carriers that are stable in serum for delivery systems to be effective both in vitro and in vivo.

It is a further object of the present invention to create complexes of RNA with rosette nanotubes that can be delivered into target cells where the RNA can then function to silence certain RNA and thereby prevent expression of an associated protein or proteins. It is a further object of the present invention to provide methods of treating individuals using a delivery system of a complex of RNA with a rosette nanotube which transfects cells of the individual in a manner to prevent expression of an associated protein or proteins. These and other objects, features, and advantages of the invention or certain embodiments of the invention will be apparent to those skilled in the art from the following disclosure and description of exemplary embodiments.

SUMMARY

Embodiments of the present disclosure are directed to methods of transfecting cells with nucleic acids or polynucleotides such as DNA or RNA, such as small RNA and its derivatives, mimic, and inhibitors. RNA according to aspects of the present disclosure includes a duplex of nucleic acids of between about 10 to about 30 nucleotides. Embodiments of the present disclosure include the formation of a composite or complex or combination of one or more nucleic acids, such as RNA, and a rosette nanotube where the one or more nucleic acids are attached to or otherwise bound to the rosette nanotube. Embodiments of the present disclosure are further directed to a product made by the process of mixing together rosette nanotubes as described herein or modules forming rosette nanotubes as described herein and one or more nucleic acids in aqueous media under conditions which cause the rosette nanotubes to combine with the one or more nucleic acids to form a complex or combination in aqueous media where the one or more nucleic acids are attached or otherwise bound through steric, ionic, covalent or other forces to the rosette nanotube.

Embodiments further include delivering the composite into living cells. Embodiments further include a method of treating an individual requiring treatment comprising administering a complex of a rosette nanotube and one or more nucleic acids to the individual in a manner to transfect cells within the individual with the one or more nucleic acids. Embodiments further include a method of treating an individual requiring treatment comprising administering a complex of a rosette nanotube and one or more nucleic acids to the individual in a manner to transfect cells within the individual with the one or more nucleic acids and wherein the cells either express the one or more nucleic acids in a therapeutic manner or the one or more nucleic acids inhibit expression of one or more proteins within the cells in a therapeutic manner.

Embodiments further include modulating gene expression or cell function by using small RNA delivered by a composite of a rosette nanotube and small RNA. The result of the modulation of gene expression or cell function can be therapeutic for particular indications.

Further aspects include delivering small RNA into cells and the use of the delivered small RNA to regulate cell signaling and function and influencing tissue or organ activities. In particular, methods are provided of introducing small RNA into cells using rosette nanotubes that advantageously do not require additional chemical modification of the components of the delivery complex. The rosette nanotube and small RNA complexes of the present disclosure are advantageous in that they are nontoxic at administration levels and they lack metals associated with known carriers.

In particular, the methods include contacting a transfection complex with one or more cells, where the transfection complex includes a rosette nanotube ("RNT") and a nucleic acid such as DNA or RNA, for example siRNA or miRNA. Rosette nanotubes or RNTs include nanotubes formed from modules having twin bases with a linker or TBL. Such rosette nanotubes may be referred to herein as "TBLs." According to this aspect, the nucleic acid is delivered into the cell. According to one aspect, the DNA is expressed by the transfected cell. According to an additional aspect, the RNA interacts with target RNA to regulate gene expression. According to one aspect, the DNA or RNA is released from the rosette nanotube after entry into the cell. According to an additional aspect, the DNA or RNA remains attached to, bound to, or complexed with or combined with the rosette nanotube.

According to one aspect, a transfection complex is produced by combining modules of a self-assembled rosette nanotube and one or more nucleic acids as DNA or RNA, for example siRNA or miRNA, in media where the modules self-assemble into a rosette nanotube which incorporates the one or more nucleic acids to form a complex of a rosette nanotube and the one or more nucleic acids. According to an additional aspect, a transfection complex is produced by combining a self-assembled rosette nanotube and one or more nucleic acids such as DNA or RNA, for example siRNA or miRNA, in media whereupon the one or more nucleic acids are incorporated into the rosette nanotube to form a complex of a rosette nanotube and one or more nucleic acids. The transfection complex may then be contacted to cells whereupon the transfection complex enters the cells. Without wishing to be bound by scientific theory, it is believes that the complex may enter cells by endocytosis. According to certain embodiments, the cells may be transformed cells, recombinant cells, malignant cells, or cells from primary cell lines. The transfection method may be performed on cells in vitro or in vivo.

The modules may be any of those known to persons of ordinary skill in the art such as G-C motifs, unmodified or modified to include moieties or sidechains, which self-assemble into helical rosette nanotubes. According to one embodiment, modules are placed into an aqueous medium where they self assemble into a substructure such as a ring structure, such as a rosette, and the ring structures then self-assemble by stacking one on top of another to form a tubular structure, commonly referred to as a nanotube. Such modules, substructures and nanometer scale molecular structures and their self-assembly is described in U.S. Pat. No. 6,696,565, Fenniri et al, *J. Am. Chem. Soc.* 2001, 123, 3854-3855, Moralez et al., *J. Am. Chem. Soc.*, 2005, 127, 8307-8309, Fine et al., *International Journal of Nanomedicine* 2009: 4 91-97; and Zhang et al., *Biomaterials* 2009; 30(7):1309-1320 each of which are hereby incorporated by reference in their entireties for all purposes.

Rosette nanotubes of the present disclosure are very stable in water and lack virus-related safety concerns and toxicity at amounts of about 1 µg/ml. See *Int. J. Nanomedicine*, 2008, 3(3):373-383; *Small*. 2008, 4(6):817-823; and *Am. J. Physiol Lung Cell Mol. Physiol.* 2005, November; 289(5): L698-708 each of which are hereby incorporated by reference in their entireties.

According to one aspect of the present disclosure, methods are provided where the self-assembly of precursers or modules incorporates the nucleic acid into or otherwise complexes the nucleic acid with, the self-assembled rosette nanotube. According to another aspect, fully assembled rosette nanotubes can be incubated with one or more or a plurality of nucleic acids and the one or more or plurality of nucleic acids can complex with the fully assembled rosette nanotube to form a composite. According to one further aspect, the one or more or plurality of nucleic acids are joined to or bound to the self-assembled rosette nanotube through steric, ionic, van der Waals, dispersion or other noncovalent interactions to form a rosette nanotube and nucleic acid complex useful as a transfection agent and in some cases in the preparation of a pharmaceutical agent to be administered to an individual. According to an additional further aspect, the one or more nucleic acids are covalently attached by methods known to those of skill in the art to the rosette nanotube to form a rosette nanotube and RNA complex useful as a transfection agent and in some cases in the preparation of a pharmaceutical agent to be administered to an individual.

According to certain aspects, rosette nanotubes are functionalized with small RNA to form a complex, for example RNA is bound to the rosette nanotube, the complex is translocated into a cell, and the intracellular small RNA is present within the cell in an amount sufficient for gene silencing resulting in the inhibition of the production of target proteins. In this aspect, the rosette nanotube is a delivery vehicle or carrier for the small RNA into a cell for RNA interference purposes.

According to an alternate aspect, nanotubes are functionalized with desired DNA to form a complex, the complex is translocated into a cell, and the desired DNA is released from the complex and incorporated into the DNA of the cell. The desired DNA is then expressed by the cell. In this aspect, the rosette nanotube is a delivery vehicle or carrier for the desired DNA into a cell for expression purposes. One of skill in the art will readily understand based on the present disclosure that target DNA, such as a gene to be expressed, can be transfected into a cell using the delivery vehicles and techniques described herein or readily available to those of skill in the art, and thereafter expressed using methods known to those of skill in the art.

Embodiments of the present invention are still further directed to compositions including rosette nanotube/nucleic acid complexes used as a vehicle for the delivery of the nucleic acid, such as RNA into a particular cell. According to certain embodiments, the rosette nanotube and RNA complexes are mixed with a pharmaceutically acceptable excipient or delivery vehicle and then delivered to the desired location and in a manner to transfect cells with the RNA, for example, for therapeutic purposes through the inhibition or alteration of the expression of a target gene. In addition, transfection kits are provided that include the rosette nanotubes of the present invention for complexing with one or more desired nucleic acids using the methods described herein pursuant to instructions and optional reagents provided in the kit to form a transfection reagent for transfection of a desired cell.

BRIEF DESCRIPTION OF THE DRAWINGS

FIGS. 9A-9F depict images of internalized RNT/SiRNA located in the cytoplasm. Confocal images of FITC-SiRNA (FIG. 9A) and HDAC4 (FIG. 9B), DAPI (FIG. 9C) as well as overlay (FIG. 9D). FIG. 9E is a 2D confocal image of FITC-SiRNA internalized by cells. FIG. 9F is a 3D confocal image of FITC-SiRNA internalized by cells.

FIGS. 15A-15D depict images of internalized RNT/miR365 molecular beacons located in the cytoplasm. Light (FIG. 15A and FIG. 15C) and fluorescent (FIG. 15B and FIG. 15D) pictures of mouse chondrocytes cultured with only GAPDH molecular beacons (FIG. 15A and FIG. 15B) or with RNT/GAPDH molecular beacons (FIG. 15C and FIG. 15D).

FIGS. 16A-16D depict images of internalized RNT/green fluorescence labeled siRNA located in the cytoplasm. Light (FIG. 16A and FIG. 16C) and fluorescent (FIG. 16B and FIG. 16D) pictures of primary human chondrocytes cultured with only siRNA (FIG. 16A and FIG. 16B) or with RNT/siRNA (FIG. 16C and FIG. 16D).

FIGS. 18A-18D depict images of internalized RNT/green fluorescence labeled siRNA located in the cytoplasm. Light (FIG. 18A and FIG. 18C) and fluorescent (FIG. 18B and FIG. 18D) pictures of human breast cancer cell line (MCF7) cultured with only siRNA (FIG. 18A and FIG. 18B) or with RNT/siRNA (FIG. 18C and FIG. 18D).

DETAILED DESCRIPTION OF CERTAIN EXEMPLARY EMBODIMENTS

The aspects, advantages and other features of the disclosure will become apparent in view of the following detailed description, which discloses various non-limiting embodiments of the disclosure. In describing embodiments of the present disclosure, specific terminology is employed for the sake of clarity. However, the disclosure is not intended to be limited to the specific terminology so selected. It is to be understood that each specific element includes all technical equivalents that operate in a similar manner to accomplish a similar purpose. Additionally, all of the citations herein are incorporated by reference in their entirety.

Embodiments of the present disclosure involve transfecting cells with one or more nucleic acids, such as DNA or RNA. RNA can be small RNA including siRNA and miRNA. In particular, disclosed herein are novel siRNA transport complexes, comprising an unexpectedly advantageous transport vehicle. Methods of the present invention include contacting a transfection complex described herein with one or more cells, where the transfection complex includes a rosette nanotube and one or more nucleic acids such as DNA and RNA, for example siRNA. The rosette nanotube is a carrier that is formed from self-assembled modules as described below and those modules recognized in the art.

Modules according to the present disclosure include compounds of Formula I below:

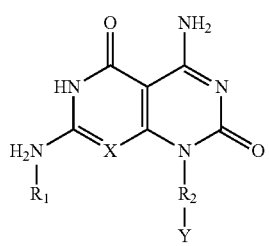

wherein X is CH or nitrogen; n is an integer of, 1, 2, 3, or 4; $R_2$ is hydrogen or a linker group for example $(CH_2)_n$ or other linker groups described herein; Y is absent when $R_2$ is hydrogen or is an amino acid or polypeptide having an amino group covalently bound to an α-carbon of the amino acid and the amino group is covalently bound to the linker group $R_2$; and $R_1$ is hydrogen or an aliphatic moiety, such as alkyl, straight or branched chain, saturated or unsaturated; and salts thereof. Preferably $R_1$ is $C_1$ to $C_{10}$ alkyl, $C_1$ to $C_5$ alkyl, $C_1$ to $C_3$ alkyl, or methyl. Compounds within the scope of the invention include those where the Y group can be connected to the linker group either by the amino group or the carboxyl group of the amino acid or polypeptide. An exemplary linker group is shown in the formula below.

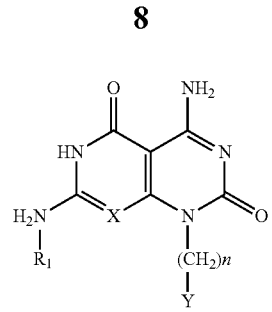

Figure 1C:
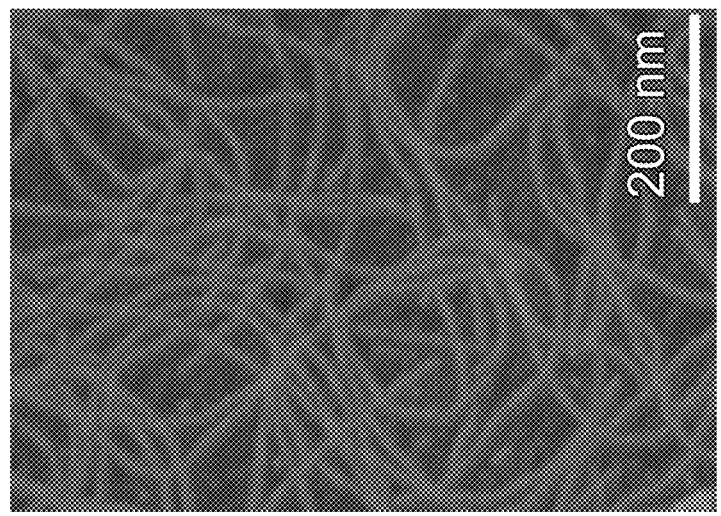
FIG. 1A shows the structure of an exemplary module used to form a rosette nanotube. Shown in schematic form in FIG. 1B is a rosette nanotube and also shown in FIG. 1C is an image of rosette nanotubes of the present disclosure.
Figure 1B:
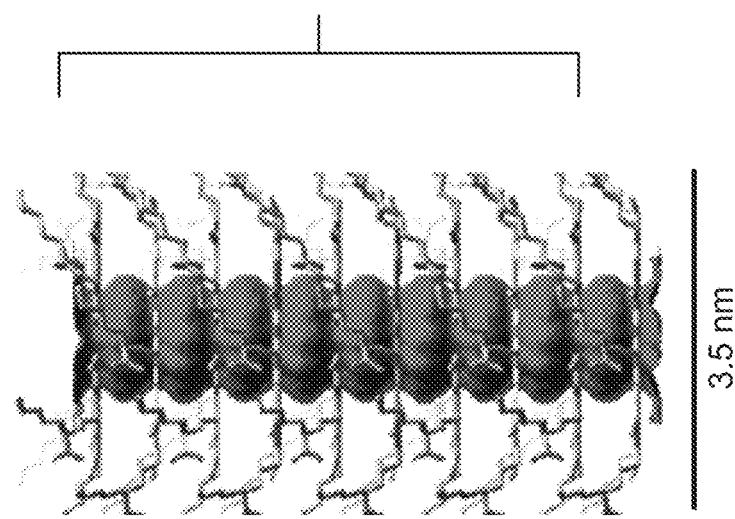
Figure 1A:
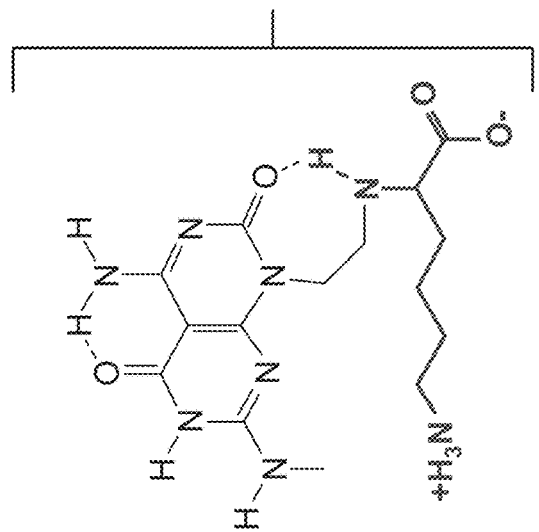

An exemplary module within the scope of formula I is shown in FIG. 1A along with a schematic representation of a nanotube (FIG. 1B) and an image of nanotubes formed from the exemplary module (FIG. 1C).

Alternative linker groups $R_2$ can join the Y group to the carbon of the $(CH_2)_n$ group or the N atom either by the amino group or the carboxyl group of the amino acid or polypeptide.

Alternative Linker moieties within the scope of the present disclosure include $NH_3^+$ and the following

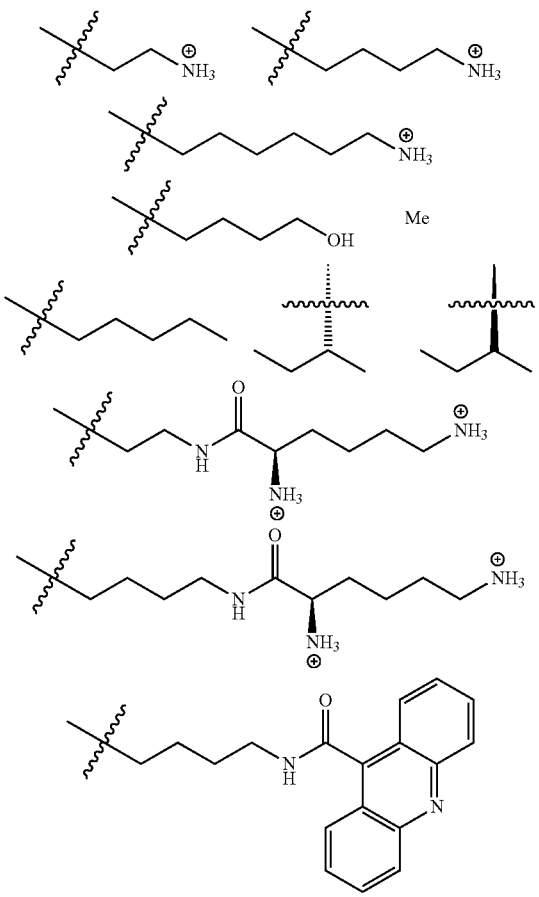

Compounds of Formula I can be prepared by the methods described in U.S. Pat. No. 6,696,565 hereby incorporated by reference herein in its entirety alone or combined with methods known to those of skill in the art.

Modules according to the present disclosure also include compounds of Formula II below:

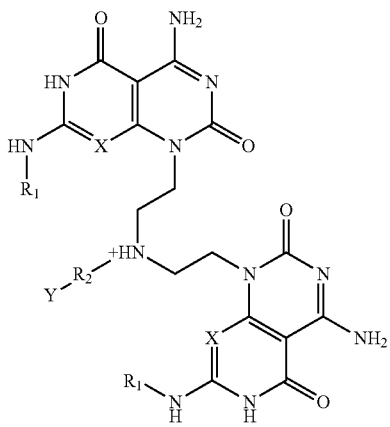

wherein X is CH or nitrogen; $R_2$ is hydrogen or a linker group for example $(CH_2)_n$ where n is an integer of, 1, 2, 3, or 4 or $(CH_2)_3CO$ other linker groups described herein; Y is absent when $R_2$ is hydrogen or is an amino acid or polypeptide having an amino group covalently bound to an α-carbon of the amino acid and the amino group is covalently bound to the linker group $R_2$; and $R_1$ is hydrogen or an aliphatic moiety, such alkyl, straight or branched chain, saturated or unsaturated; and salts thereof. Preferably $R_1$ is $C_1$ to $C_{10}$ alkyl, $C_1$ to $C_5$ alkyl, $C_1$ to $C_3$ alkyl, or methyl. An exemplary linker group is shown in the formula below.

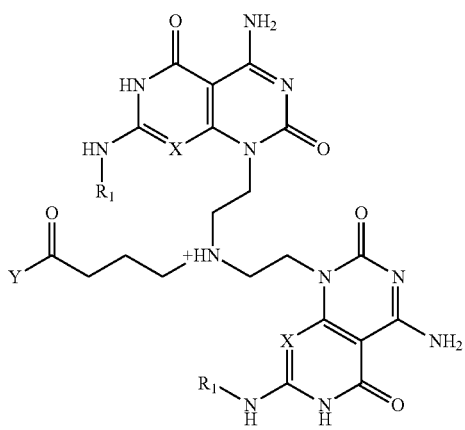

Compounds within the scope of the present disclosure include those where the Y group can be connected to the linker group either by the amino group or the carboxyl group of the amino acid or polypeptide. Alternative linker groups $R_2$ connecting the $NH^+$ group and the Y group include

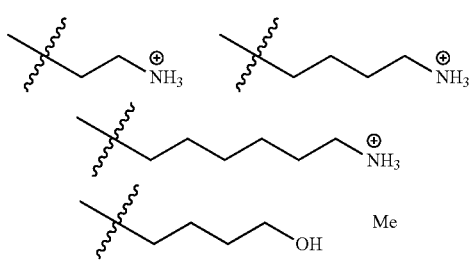

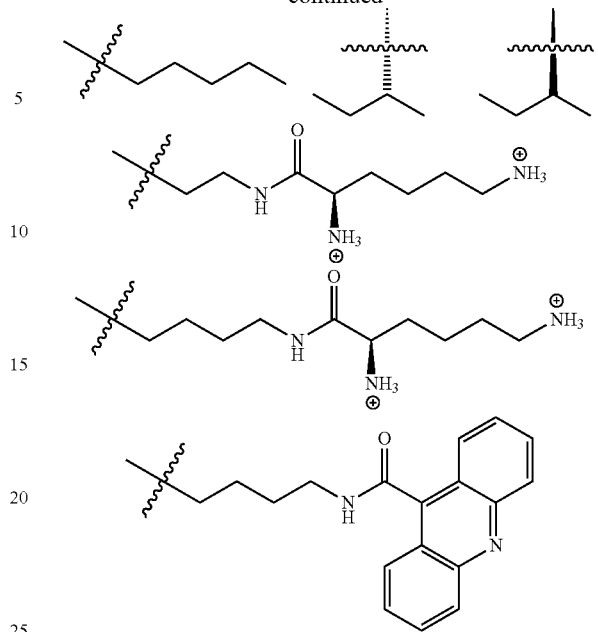

According to certain aspects of the present disclosure, the structure of Formula II is referred to as a twin base with a linker (TBL) or twin base linkers insofar as two similar double ring structures are present as shown in Formula II and are linked to an amino acid or polypeptide. However, it is to be understood that the two double ring structures need not be identical insofar as they may have different X and $R_1$ groups.

The term "amino acid" is inclusive of the 20 common amino acids, as well as "nonstandard amino acids," for example, D-amino acids and chemically (or biologically) produced derivatives of "common" amino acids, including for example, β-amino acids. Accordingly, amino acids according to the present disclosure include the commonly known amino acids such as glycine (Gly, G), alanine (Ala, A), valine (Val, V), leucine (Leu, L), isoleucine (Ile, I), proline (Pro, P), hydroxyproline, phenylalanine (Phe, F), tyrosine (Tyr, Y), tryptophan (Trp, W) cysteine (Cys, C), methionine (Met, M) serine (Ser, S), o-phosphoserine, threonine (Thr, T), lysine (Lys, K), arginine (Arg, R), histidine (His, H), aspartate (Asp, D), glutamate (Glu, E), γ-carboxyglutamate, asparagine (Asn, N), glutamine (Gln, Q) and the like. Amino acids also include stereoisomers thereof and compounds structurally similar to the amino acids or modifications or derivatives thereof. Exemplary amino acids within the scope of the present disclosure include lysine, arginine, serine, glycine, aspartate and the like.

The term "peptide" is inclusive of both straight and branched amino acid chains, as well as cyclic amino acid chains, which comprise at least 2 amino acid residues. The terms "peptide" and "polypeptide" are used interchangeably herein. Accordingly, polypeptides according to the present disclosure include two or more amino acids covalently linked together. According to one aspect, the two or more amino acids are covalently linked together at least in part by one or more peptide bonds.

According to aspects of the present disclosure, modules (compounds) according to Formula I and Formula II self-assemble into substructures also called supermacrocycles which themselves will self-assemble into nanometer scale architectures or structures such as discrete nanotubular assemblies in water or aqueous solutions. Supermacrocycles are defined herein as being a number of organic molecules covalently or noncovalently bound together so as to form a ring structure. For example, compounds of Formula I will self-assemble into a 6-mer ring structure, sometimes referred to as a rosette. The process of forming nanotubes with the modules of the present disclosure is hierarchical. In particular, the modules of the present invention first self-assemble into supermacrocycles, and then the supermacrocycles self-assembly into nanotubes. Such self-assembly is described in U.S. Pat. No. 6,696,565. For the compounds of Formula II referred to as twin base linkers, the compounds will also assemble into a 6-mer ring structure. However, a single supermacrocycle formed will include two base layers owing to the presence of the two bases in each of the compound of Formula II.

According to preferred aspects of the present disclosure, the compounds of Formula I and Formula II include low molecular weight synthetic DNA base analogues referred to by the nomenclature G∧C. See Fenniri et al, *J. Am. Chem. Soc.* 2001, 123, 3854-3855. The G∧C moiety, referred to as a single G∧C motif, possess the Watson-Crick donor-donor-acceptor of guanine and the acceptor-acceptor-donor of cytosine and undergoes a self-assembly process, fueled by an array of hydrogen bonds, to produce a six-membered supermacrocycle or rosette. Stacking of these rosettes produced a nanotube of very high aspect ratio. Compounds within the scope of the present invention include a twin G∧C motif denoted as $(G\wedge C)_2$. Like the single G∧C motif, the twin G∧C motif $(G\wedge C)_2$ also possesses the Watson-Crick donor-donor-acceptor of guanine and the acceptor-acceptor-donor of cytosine and undergoes a self assembly process, fueled by an array of hydrogen bonds, to produce a six-membered supermacrocycle or ring structure (rosette) of twin configuration. Stacking of these twin rosettes produces a nanotube of very high aspect ratio and higher stability.

It should be understood that the above described Formula I and Formula II demonstrate that electrostatic, stacking and hydrophobic interactions can be effectively orchestrated by hydrogen bonds to direct the hierarchical assembly and organization of helical nanotubular architectures in an aqueous milieu. Helical nanotubular architectures within the scope of the present invention include those formed entirely from compounds of Formula I. Helical nanotubular architectures within the scope of the present invention include those formed entirely from compounds of Formula II. Further, helical nanotubular architectures within the scope of the present invention include those formed from one or more of the compounds of Formula I and one or more of the compounds of Formula II. For example, a supermacrocycle ring substructure having particular amino acid or polypeptide side chains formed from the compounds of Formula I can be stacked with a supermacrocycle ring substructure having particular amino acid or polypeptide side chains formed from compounds of Formula II. The rosette substructures formed from the compounds of Formula I and Formula II can be stacked in any desired sequence to form nanotubular structures of the present invention. Utilizing this aspect of the present invention, a wide variety of structurally different modules (i.e. molecules) can be synthesized and self-assembled into supermacrocycles and then nanotubular structures according to methods of the present invention.

According to certain aspects of the present disclosure, nanotubes range in lengths between about 1 nm and about 999 microns, about 1 nm to about 500 nm, about 10 nm to about 300 nm, or about 20 nm to about 100 nm. The nanotubes range in diameters between about 1 angstrom and about 100 nm, about 1 nm to about 30 nm, or from about 3 nm to about 15 nm. The openings or inner diameters through the nanotubes range in diameters between about 1 angstrom and about 100 nm, about 1 nm to about 30 nm, or from about 3 nm to about 15 nm. According to certain embodiments, the opening or inner diameter through the nanotube has a diameter of about 1 nm. According to certain embodiments, the nanotubes formed from the twin base linkers of formula II have a different opening or inner diameter compared to nanotubes formed from the compounds of formula I. This aspect which allows for the incorporation into the nanotube of different sizes of agents, such as nucleic acids.

According to certain preferred aspects of the present invention, a nanotube is prepared from single base ring structures and twin base ring structures in any desired order. The nanotube can have one or more single base ring structures and one or more twin base ring structures. Likewise, a nanotube within the scope of the present invention can include a plurality of single base ring structures formed from compounds of Formula I and a plurality of twin base ring structures formed from compounds of Formula II stacked together, i.e. one next to the other via hydrogen bonding, to form the nanotube.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the invention may comprise natural nucleic acid sequences and variants thereof, artificial nucleic acid sequences, or a combination of such sequences. As used herein, one of skill in the art will understand that the term "nucleic acid probe" includes probes known as molecular beacons which include synthetic oligonucleotide hybridization probes that can report the presence of specific nucleic acids in homogenous solutions or in cells. Species of molecular beacons include hairpin shaped molecules with an internally quenched fluorophore whose fluorescence is restored when they bind to a target nucleic acid sequence. Technically, molecular beacons can be designed to target any gene and can be linked with fluorescent molecules of different fluorescence wavelengths.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more nonstandard nucleotide(s), nucleotide analog(s) and/or modified nucleotides.

Examples of modified nucleotides include, but are not limited to 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety, sugar moiety or phosphate backbone.

According to certain aspects, nucleic acids or polypeptides includes small RNA being a duplex of between about 10 to about 30 nucleic acids, between about 15 to about 25 nucleic acids and between about 20 to about 23 nucleic acids, and any values and ranges in between whether overlapping or not. The small RNA can be formed by one or more oligonucleotides. Small RNA includes RNA commonly referred to as interference RNA, dsRNA, ssRNA, saRNA, siRNA or miRNA or their derivatives, analogs, mimics and inhibitors. According to certain aspects, siRNA is involved in the RNA interference (RNAi) pathway, where it interferes with the expression of a specific gene. In addition to their role in the RNAi pathway, siRNAs also act in the RNAi-related pathways. siRNA within the scope of the present disclosure includes double stranded RNA of about 21 nucleotides with a 2 nucleotide 3' overhang on either end of the siRNA. Each siRNA strand has a 5' phosphate group and a 3' hydroxyl (—OH) group. The structure is the result of processing by dicer, an enzyme that converts either long dsRNAs or small hairpin RNAs into siRNAs. Particular exemplary sequences of siRNA are readily available to those of skill in the art through published literature and siRNA is commercially available from, for example, Qiagen. It is to be understood that the present disclosure is not to be limited to any particular siRNA sequence, but rather the present disclosure broadly describes the incorporation of siRNA into or with rosette nanotubes. One of skill in the art will readily recognize that all siRNA sequences, given the similar structure and function of covalently connected nucleotides, can be incorporated into or complexed with rosette nanotubes using the methods described herein and that an exhaustive listing of publicly known siRNA sequences need not be provided herein.

According to additional aspects, DNA includes any DNA desired to be expressed by a cell. DNA includes genes having known functions and expressing known proteins. Likewise, DNA suitable for transfecting a cell will be apparent to those of skill in the art of transfection and gene expression.

The present disclosure is directed to methods of forming a transfection complex, for example, by mixing one or more nucleic acids with fully formed rosette nanotubes or modules that self-assemble into rosette nanotubes, such as the compounds of formula I or formula II. According to one aspect, fully formed rosette nanotubes in the form of a powder is dissolved in water and heated to boiling. The solution is then cooled to room temperature. One or more nucleic acids in the form of a solution is then added to the solution of nanotubes at a suitable temperature and for a suitable period of time until a complex of the nanotube and one or more nucleic acids forms. Suitable ratios of the nucleic acid to nanotube include about 0.01:1 (wt/wt) to about 1:0.1 (wt/wt).

The invention is further directed to transfection complexes, which include small RNA, such as siRNA and a rosette nanotube. Transfection complexes in accordance with the present invention may include any of the rosette nanotubes of the present invention in combination with small RNA known to those of skill in the art.

According to certain aspects, cells within the scope of the present invention that can be transfected include osteoblasts, fibroblasts, endothelial cells, stem cells, keratinocytes, cardiac myocytes, chondrocytes, synoviocytes, mesenchymal stem cells, neural stem cells, islet cells, hepatocytes, smooth muscle cells, urothelial cells, neurons, Schwann cells, microgial cells, cancerous and non cancerous cells, epithelial cells, endothelial cells, myofibroblasts, osteoclasts, macrophages, leukocytes, osteocytes, astrocytes etc. and the like. Additional cells include bacterial cells such as *Staphylococcus aureus, Staphylococcus epidermis, Pseudomonas aeruginosa*, MRSA, *E. coli, candida* (yeast), *Candida albacans, Streptococcus pneumoniae, Neisseria meningitides, Haemophilus influenzae, Streptococcus agalactiae, Listeria monocytogenes, Mycoplasma pneumoniae, Chlamydia pneumoniae, Legionella pneumophila, Mycobacterium, tuberculosis, Streptococcus pyogenes, Chlamydia trachomatis, Neisseria gonorrhoeae, Treponema pallidum, Ureaplasma urealyticum, Haemophilus ducreyi, Helicobacter pylori, Campylobacter jejuni, Salmonella, Shigella, Clostridium*, Enterobacteriaceae, *Staphylococcus saprophyticus* and the like. The above list is intended to be exemplary and not exhaustive. One of skill in the art will readily be able to identify additional cells within the scope of the present disclosure.

According to aspects of the present disclosure, composites of rosette nanotubes and small RNA can be combined with a pharmaceutically acceptable agent and administered as a delivery composition to an individual for therapeutic purposes. As used herein, a "pharmaceutically acceptable agent" (such as a salt, carrier, excipient or diluent) is a component which (1) is compatible with the RNT/small RNA composites in that it can be included in the delivery composition without eliminating the capacity of the RNT/small RNA composites to transfect cells and deliver small RNA; and (2) where the delivery composition is intended for therapeutic uses, is suitable for use with an animal (e.g., a human) without undue adverse side effects, such as toxicity, irritation, and allergic response. Side effects are "undue" when their risk outweighs the benefit provided by the pharmaceutical agent.

The term "small RNA" is used as it is in the art, and includes a duplex of RNA (30 bases or less in each strand) that targets mRNA. Small RNA may be chemically or enzymatically synthesized. Small RNA in accordance with the present invention may be incorporated and then activated in RISC(RNA-induced silencing complex).

A "therapeutically effective amount" is an amount necessary to prevent, delay or reduce the severity of the onset of disease, or an amount necessary to arrest or reduce the severity of an ongoing disease, and also includes an amount necessary to enhance normal physiological functioning.

The word "transfect" is broadly used herein to refer to introduction of an exogenous compound, such as a polynucleotide sequence, into a prokaryotic or eukaryotic cell; the term includes, without limitation, introduction of an exogenous nucleic acid into a cell, which may result in a permanent or temporary alteration of genotype in an immortal or non-immortal cell line. Accordingly, embodiments of the present disclosure include the introduction of a polynucleotide sequence to either be expressed or to inhibit expression of a target gene.

In general, a cell to be transfected includes, but is not limited to, any animal, plant or bacterial cell that is susceptible to intracellular delivery of DNA or RNA such as siRNA using the transfection complex of the present invention either in vitro or in vivo. For example, cells from different species such as human, mouse, rat, pig, chicken, etc. may be used according to the present disclosure. Likewise, cells from different tissues or organs, such as liver, fibroblast, beast cells, macrophages from the immune system, astrocytes from the neuronal system may be used. Likewise, primary cells obtained directly from animals, plants or bacteria may be used and cell lines, such as commercially available immortalized cell, may be used. Likewise, normal cells may be used and diseased cells may be used, such as cancer cells. For example, suitable cellular targets include, without limitation, epithelial cells, endothelial cells, keratinocytes, fibroblasts, muscle cells, hepatocytes, blood cells such as T lymphocytes, B lymphocytes, monocytes, macrophages, neutrophils, eosinophils, megalaryocytes, granulocytes, various stem or progenitor cells, in particular hematopoietic stem or progenitor cells, e.g., as obtained from bone marrow, umbilical cord blood, peripheral blood, fetal liver, and the like. In certain aspects, the cell is selected from the group consisting of lung cells, liver cells, endothelial cells, muscle cells, skin cells, hematopoietic stem cells and tumor cells.

According to certain embodiments, the cells include one or more cells selected from the group consisting of transformed, recombinant, malignant, and primary cell lines. It is believed that the rosette nanotubes of the present invention will be effective as carriers of DNA or RNA such as siRNA in most, if not all cell types and cell lines. Since complexes of the rosette nanotubes and nucleic acids are composed of covalently bound base pairs, one of skill would expect that such complexes will be universally recognized by all cell types for transfecting purposes.

Methods of transfecting cells in accordance with the present invention may also include forming the transfection complex by combining in aqueous media the modules of the rosette nanotube and one or more DNA sequences and/or one or more RNA sequences. The complex is allowed to form. Cells are then contacted with the complex. According to one aspect, one of skill in the art will recognize from the benefit of the present disclosure that doses, concentrations, ratios and conditions of RNT/nucleic acids incorporation can be within ranges. For example, between about 1 μL to about 100 μL, for example 10 μL, of 1 mg/mL RNTs can be mixed with about 1 μL to about 100 μL, for example 20 μL, of 5 μM nucleic acids, such as siRNA, miRNA, nucleic acid probes or other nucleic acids, at a temperature of between about 0° C. to about 37° C. for between about 0.5 hours to about 48 hours and added into 1 mL cell culture medium for transfection. For example, the combination of RNT and nucleic acids can be maintained at 4° C. for 24 hours or can be maintained at room temperature for two hours. Mixing can be accomplished by simple mixing, mixing while heating to about 60° C. to about 100° C., sonication or other methods known to those of skill in the art. If heated, the combination may then be subjected to a temperature of between about 0° C. to about 37° C. for between about 0.5 hours to about 48 hours to result in formation or assembly of the nanotube/nucleic acid complex.

The present invention also provides methods of treating diseases comprising using the complexes or compositions of the present invention. In particular, methods are provided for treating a patient having a disease, by administering to the patient a therapeutically effective amount of a complex or composition of the present invention. For in vivo therapies based on local injection (e.g., intratumoral, intramuscularly, into the peritoneal cavity, intracardiac, and aerosolized treatments) the RNT/small RNA complex is advantageously water soluble and so may be administered as an aqueous injection.

In accordance with certain examples, complexes of the present invention can be incorporated into pharmaceutical compositions suitable for administration. Such compositions typically comprise the complexes disclosed here and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In accordance with certain examples, a pharmaceutical composition of the invention is formulated to be compatible with its intended route of administration. Such pharmaceutical compositions may be administered by inhalation, transdermally, orally, rectally, transmucosally, intestinally, parenterally, intramuscularly, subcutaneously, intravenously or other suitable methods that will be readily selected by the person of ordinary skill in the art, given the benefit of this disclosure. For example, solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Also encompassed are methods for treating a patient having a disease, by administering to the patient cells that have been transfected by the methods disclosed herein. An aspect of an ex vivo delivery method of the present invention may include for example, (i) removing a cell from a subject; (ii) introducing siRNA into a cell by contacting the cell with a delivery composition (transfection complex or composition comprising such a transfection complex) comprising siRNA and a rosette nanotube; and (iii) reintroducing the cell into the subject. In addition, nanotubes having nucleic acids complexed therewith as described herein may be delivered in vivo to an individual in need of treatment where the nanotubes having nucleic acids complexed therewith enter cells within the individual and the nucleic acids regulate cellular expression of proteins. For example the nucleic acids may silence genes in a therapeutic manner to the extent that a protein is not expressed resulting in treatment or the nucleic acids may be expressed by the cell to produce proteins in a therapeutic manner resulting in treatment.

Examples of genetic and/or non-neoplastic diseases potentially treatable with the complex, compositions, and methods include, but are not limited to the following: adenosine deaminase deficiency; purine nucleoside phosphorylase deficiency; chronic granulomatous disease with defective p47phox; sickle cell with HbS, β-thalassemia; Faconi's anemia; familial hypercholesterolemia; phenylketonuria; ornithine transcarbamylase deficiency; apolipoprotein E deficiency; hemophilia A and B; muscular dystrophy; cystic fibrosis; Parkinsons, retinitis pigmentosa, lysosomal storage disease (e.g., mucopolysaccharide type 1, Hunter, Hurler and Gaucher), diabetic retinopathy, human immunodeficiency virus disease virus infection, acquired anemia, cardiac and peripheral vascular disease, osteoporosis and arthritis. In some of these examples of diseases, the therapeutic gene may encode a replacement enzyme or protein of the genetic or acquired disease, an antisense or ribozyme molecule, a decoy molecule, or a suicide gene product.

Ex vivo and in vivo gene therapy with siRNA could also be used in cancer. These RNAi applications toward cancer include, but are not limited to, 1) reducing expression of growth factors, reducing proteins that augment the cell cycle (e.g., Raf-1, PI-3 kinase), growth factor receptors (e.g., EGFR, Her-2), or proteins critical for supporting cells of the tumor (e.g., VEGF, VEGFR1-2 for tumor endothelial cells); 2) targeting or reducing expression of factors that are anti-apoptotic (e.g., BCL-2); and 3) targeting proteins or enzymes that reduce immune activation toward tumor.

Cancers or neoplasms contemplated within the scope of the disclosure include, but are not limited to, carcinomas (i.e., malignant tumors derived from epithelial cells such as, for example, common forms of breast, prostate, lung and colon cancer), sarcomas (i.e., malignant tumors derived from connective tissue or mesenchymal cells), lymphomas (i.e., malignancies derived from hematopoietic cells), leukemias (i.e., malignancies derived from hematopoietic cells), germ cell tumors (i.e., tumors derived from totipotent cells. In adults most often found in the testicle or ovary; in fetuses, babies and young children, most often found on the body midline, particularly at the tip of the tailbone), blastic tumors (i.e., a typically malignant tumor which resembles an immature or embryonic tissue) and the like.

Examples of specific neoplasms intended to be encompassed by the present invention include, but are not limited to, acute lymphoblastic leukemia; myeloid leukemia, acute myeloid leukemia, childhood; adrenocortical carcinoma; AIDS-related cancers; AIDS-related lymphoma; anal cancer; appendix cancer; astrocytoma (e.g., cerebellar, cerebral); atypical teratoid/rhabdoid tumor; basal cell carcinoma; bile duct cancer, extrahepatic; bladder cancer; bone cancer, osteosarcoma and malignant fibrous histiocytoma; brain tumor (e.g., brain stem glioma, central nervous system atypical teratoid/rhabdoid tumors, central nervous system embryonal tumors, cerebellar astrocytoma, cerebral astrocytoma/malignant glioma, craniopharyngioma, ependymoblastoma, ependymoma, medulloblastoma, medulloepithelioma, pineal parenchymal tumors of intermediate differentiation, supratentorial primitive neuroectodermal tumors and/or pineoblastoma, visual pathway and/or hypothalamic glioma, brain and spinal cord tumors); breast cancer; bronchial tumors; Burkitt lymphoma; carcinoid tumor (e.g., gastrointestinal); carcinoma of unknown primary; central nervous system (e.g., atypical teratoid/rhabdoid tumor, embryonal tumors (e.g., lymphoma, primary); cerebellar astrocytoma; cerebral astrocytoma/malignant glioma; cervical cancer; chordoma; chronic lymphocytic leukemia; chronic myelogenous leukemia; chronic myeloproliferative disorders; colon cancer; colorectal cancer; craniopharyngioma; cutaneous T-cell lymphoma; embryonal tumors, central nervous system; endometrial cancer; ependymoblastoma; ependymoma; esophageal cancer; Ewing family of tumors; extracranial germ cell tumor; extragonadal germ cell tumor; extrahepatic bile duct cancer; eye cancer (e.g., intraocular melanoma, retinoblastoma); gallbladder cancer; gastric cancer; gastrointestinal tumor (e.g., carcinoid tumor, stromal tumor (gist), stromal cell tumor); germ cell tumor (e.g., extracranial, extragonadal, ovarian); gestational trophoblastic tumor; glioma (e.g., brain stem, cerebral astrocytoma); hairy cell leukemia; head and neck cancer; hepatocellular cancer; Hodgkin lymphoma; hypopharyngeal cancer; hypothalamic and visual pathway glioma; intraocular melanoma; islet cell tumors; Kaposi sarcoma; kidney cancer; large cell tumors; laryngeal cancer (e.g., acute lymphoblastic, acute myeloid); leukemia (e.g., acute myeloid, chronic lymphocytic, chronic myelogenous, hairy cell); lip and/or oral cavity cancer; liver cancer; lung cancer (e.g., non-small cell, small cell); lymphoma (e.g., AIDS-related, Burkitt, cutaneous Tcell, Hodgkin, non-Hodgkin, primary central nervous system); macroglobulinemia, Waldenström; malignant fibrous histiocytoma of bone and/or osteosarcoma; medulloblastoma; medulloepithelioma; melanoma; merkel cell carcinoma; mesothelioma; metastatic squamous neck cancer; mouth cancer; multiple endocrine neoplasia syndrome; multiple myeloma/plasma cell neoplasm; mycosis fungoides; myelodysplastic syndromes; myelodysplastic/myeloproliferative diseases; myelogenous leukemia (e.g., chronic, acute, multiple); myeloproliferative disorders, chronic; nasal cavity and/or paranasal sinus cancer; nasopharyngeal cancer; neuroblastoma; non-Hodgkin lymphoma; non-small cell lung cancer; oral cancer; oral cavity cancer, oropharyngeal cancer; osteosarcoma and/or malignant fibrous histiocytoma of bone; ovarian cancer (e.g., ovarian epithelial cancer, ovarian germ cell tumor, ovarian low malignant potential tumor); pancreatic cancer (e.g., islet cell tumors); papillomatosis; paranasal sinus and/or nasal cavity cancer; parathyroid cancer; penile cancer; pharyngeal cancer; pheochromocytoma; pineal parenchymal tumors of intermediate differentiation; pineoblastoma and supratentorial primitive neuroectodermal tumors; pituitary tumor; plasma cell neoplasm/multiple myeloma; pleuropulmonary blastoma; primary central nervous system lymphoma; prostate cancer; rectal cancer; renal cell cancer; renal, pelvis and/or ureter, transitional cell cancer; respiratory tract carcinoma involving the nut gene on chromosome 15; retinoblastoma; rhabdomyosarcoma; salivary gland cancer; sarcoma (e.g., Ewing family of tumors, Kaposi, soft tissue, uterine); Sézary syndrome; skin cancer (e.g., non-melanoma, melanoma, merkel cell); small cell lung cancer; small intestine cancer; soft tissue sarcoma; squamous cell carcinoma; squamous neck cancer with occult primary, metastatic; stomach cancer; supratentorial primitive neuroectodermal tumors; T-cell lymphoma, cutaneous; testicular cancer; throat cancer; thymoma and/or thymic carcinoma; thyroid cancer; transitional cell cancer of the renal, pelvis and/or ureter; trophoblastic tumor; unknown primary site carcinoma; urethral cancer; uterine cancer, endometrial; uterine sarcoma; vaginal cancer; visual pathway and/or hypothalamic glioma; vulvar cancer; Waldenström macroglobulinemia; Wilms tumor and the like. For a review, see the National Cancer Institute's Worldwide Website (cancer.gov/cancertopics/alphalist). One of skill in the art will understand that this list is exemplary only and is not exhaustive, as one of skill in the art will readily be able to identify additional cancers and/or neoplasms based on the disclosure herein.

Recombinant cells may be produced using the complexes of the present invention. Resulting recombinant cells can be delivered to a subject by various methods known in the art. In certain embodiments, the recombinant cells are injected, e.g., subcutaneously. In other embodiments, recombinant skin cells may be applied as a skin graft onto a patient. Recombinant blood cells (e.g., hematopoietic stem or progenitor cells) are preferably administered intravenously. The cells can also be encapsulated in a suitable vehicle and then implanted in the subject (see, e.g., Dionne et al. PCT Publication WO92/19195, dated Nov. 12, 1992). The amount of cells administered depends on a variety of factors known in the art, for example, the desired effect, subject state, rate of expression of the chimeric polypeptides, etc., and can readily be determined by one skilled in the art.

EXAMPLES

The following examples are specific embodiments of the present invention but are not intended to limit it.

Example 1

Cell Culture of Chondrocytes

Primary mouse chondrocytes were isolated from the rib cage of 5 days old mice. Human chondrocyte cell line C28I2 and ADTC5 mouse chondrocyte were incubated in growth media including DMEM/F12 supplement with 10% fetal calf serum.

Example 2

Preparation of RNT/Nucleic Acid Complexes

According to an aspect of the present disclosure, nucleic acids are incorporated or complexed with rosette nanotubes formed from the compounds of Formula I (RNTs) or with rosette nanotubes formed from the compounds of Formula II (TBLs). RNTs were formed using a compound of Formula I where $R_1$ is methyl, X is nitrogen, $R_2$ is the linker $(CH_2)_2$ and Y is lysine. TBLs were formed using a compound of Formula II where $R_1$ is methyl, X is nitrogen, $R_2$ is the linker $(CH_2)_3$ and Y is $NH_3^+$. Specifically and without limitation, 1 mg of modules of rosette nanotubes in powder form were dissolved in 1 ml of distilled water and sonicated and heated to boiling so that rosette nanotubes were formed. The structures of the rosette nanotubes were described in U.S. Pat. No. 6,696,565; Fenniri, J. Am. Chem. Soc, 2001, 123, 3854-3855; and Moralez, J. Am. Chem. Soc. 2005, 127, 8307-8309 each of which are hereby incorporated by reference in their entireties. One particular module forming the rosette nanotube is shown in FIGS. 1A-1C. The solution was cooled to room temperature. 2 µl of the solution was mixed with 45 µl of an siRNA solution containing 0.16 nmol FITC labeled siRNA (Qiagen, Hilden, Germany) at 4° C. overnight.

Alternatively, modules of rosette nanotubes as described above in powder form are combined with a water and a solution of an siRNA solution containing FITC labeled siRNA (Qiagen, Hilden, Germany) are sonicated and heated to boiling. The combination is then cooled to room temperature and maintained at 4° C. overnight.

Alternatively, purified rosette nanotubes were sterilized in boiled water. 0.5 ng/ml rosette nanotubes were incubated with 100 nmol FITC labeled scrambled siRNA or HDAC4 siRNAs (Qiagen, Hilden, Germany) at 4° C. for overnight.

Figure 2A:
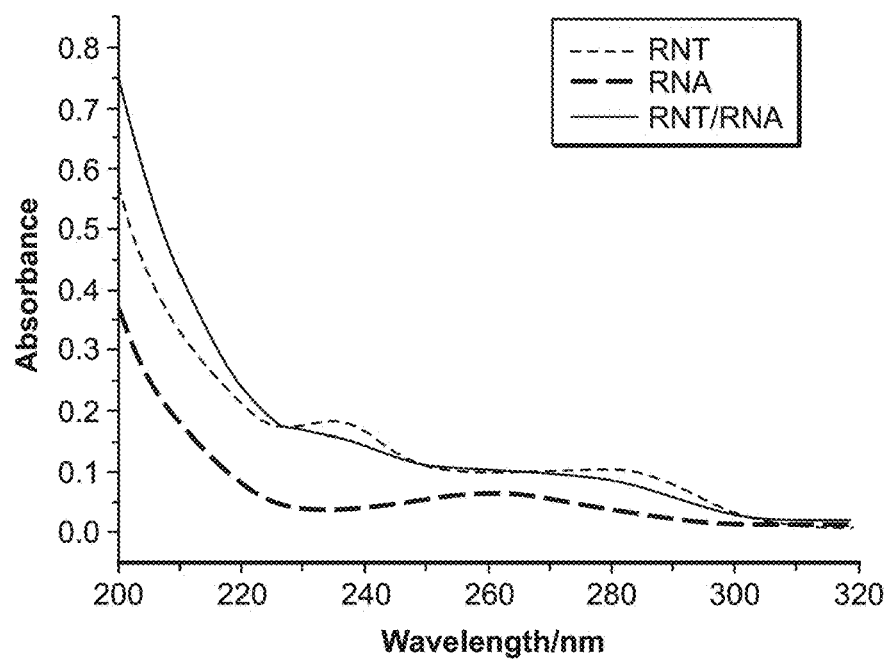
FIG. 2A is a graphical comparison of RNT (rosette nanotubes), RNA, RNT/RNA composites.
Figure 2B:
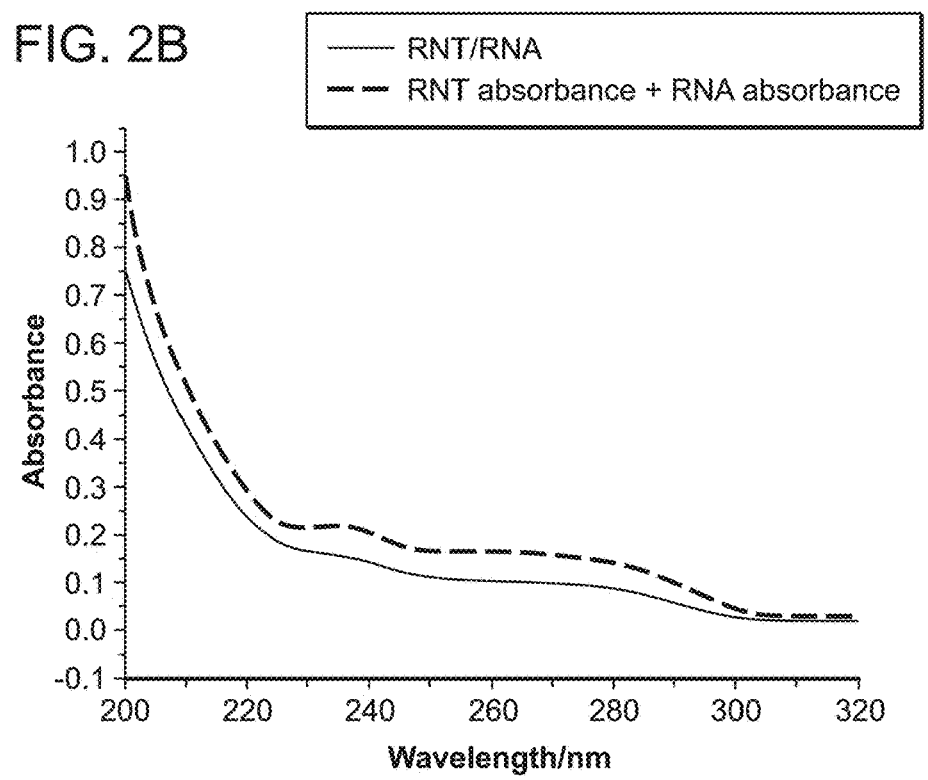
FIG. 2B is a graphical comparison of RNT/RNA composites and the sum of absorbance RNTs and RNA in UV-vis spectroscopy.

Small RNAs were incorporated into and complexed with rosettes nanotubes. 1 µL of 50 µM scrambled siRNA was incorporated with 5 µL of 1 mg/mL RNTs according to the method described above. Then, the solution was added into 1 mL water for UV-Vis measurement. Solutions of siRNA only and RNT only were also prepared at the same concentration as above for UV-Vis measurement. As shown in FIGS. 2A-2B, the incorporation was determined by a lower light absorbance of the RNT/siRNA composites in UV-Vis spectroscopy compared with the total absorbance of siRNA and RNTs tested separately. This demonstrated that the small RNA and the RNTs were physically mixed together and with their bases also packed together.

Figure 3A:
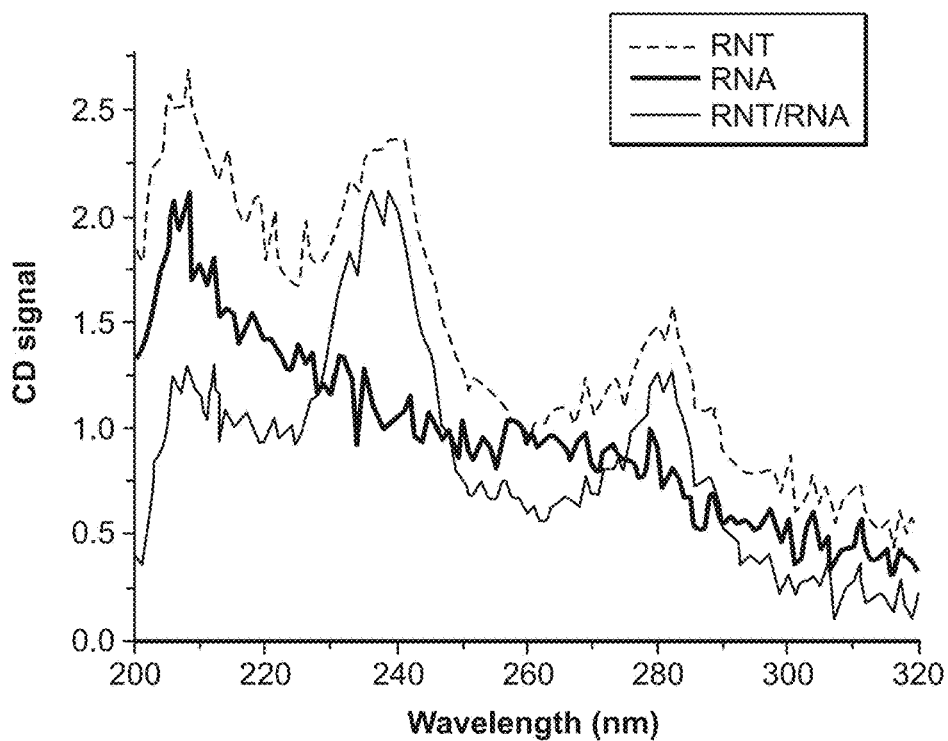
FIG. 3A is a graphical comparison of RNT, RNA, RNT/RNA composites.
Figure 3B:
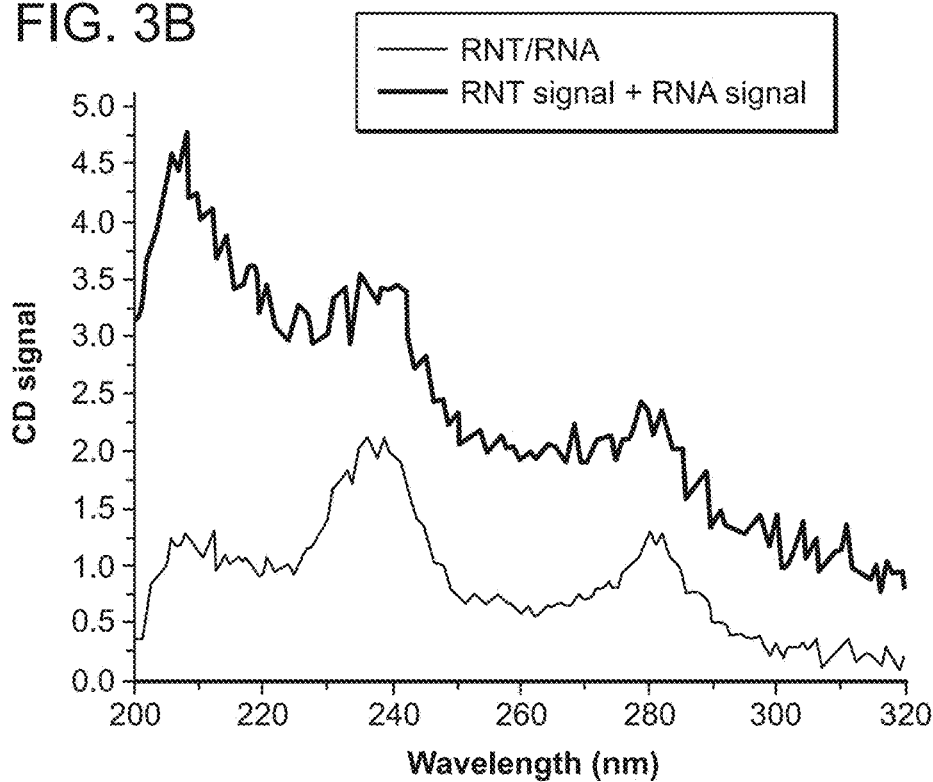
FIG. 3B is a graphical comparison of RNT/RNA composites and the sum of absorbance RNTs and RNA in CD spectroscopy.

Moreover, a CD spectroscopy was applied to detect the change in the chirality of RNT/siRNA composites and to verify their physical incorporation. 1 µL of 50 µM scrambled siRNA was incorporated with 5 µL of 1 mg/mL RNTs according to the method described above. Then, the solution was added into 1 mL water for CD spectroscopy. Solutions of siRNA only and RNT only were also prepared at the same concentration as above for the experiment. As shown in FIGS. 3A-3B, a change of molecular chirality demonstrated the incorporation between RNTs and siRNA.

Figure 4A:
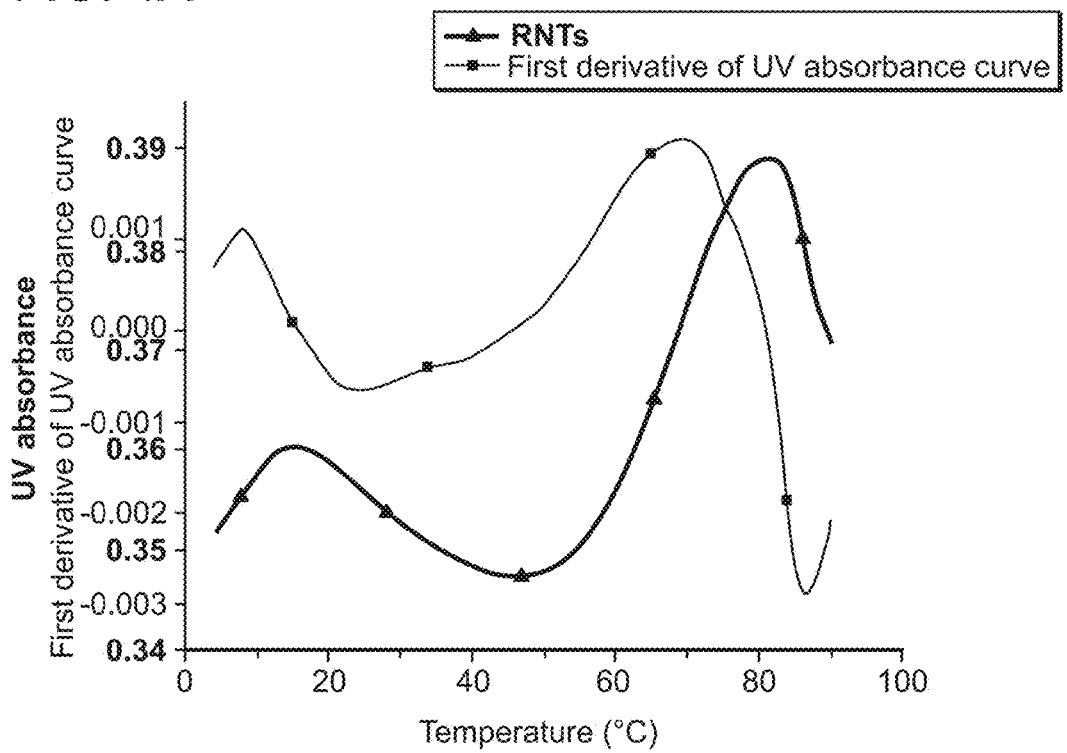
FIG. 4A is a graphical comparison of RNT denaturation curve and FIG. 4B is a graphical comparison of RNT/RNA composites denaturation curve with the first derivative of such curve demonstrating the denaturation temperature of RNT/RNA composites.
Figure 4B:
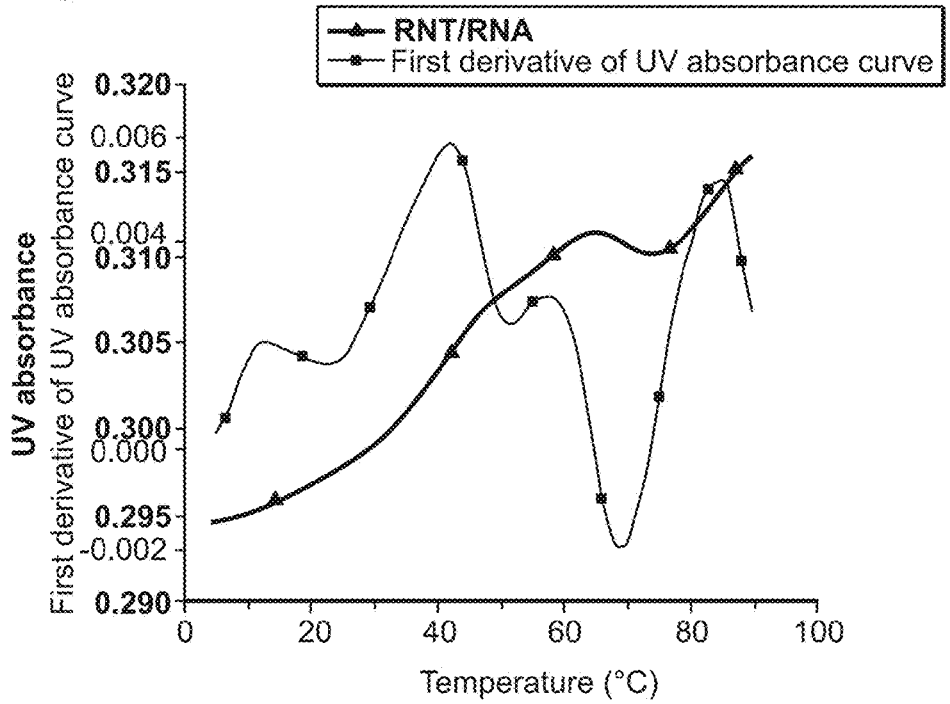

Thermo analysis experiments were conducted to determine disassembly of the siRNAs from RNTs. 1 µL of 50 µM scrambled siRNA was incorporated with 5 µL of 1 mg/mL RNTs as the method mentioned above. Then, the solution was added into 0.3 mL water for thermo analysis. Temperatures increased from 4° C. to 99° C. with 1 minute equilibrium time at every temperature. RNT only solution was also prepared at the same concentration as above. As shown in FIGS. 4A-4B, transition temperatures of RNTs in RNT/siRNA composites in thermo analysis experiments were lower than the melting temperatures of RNTs alone. This demonstrated the ability of siRNAs to disassemble from RNTs so that after delivery into a cell, siRNA could release from RNTs for desired functions.

Figure 5:
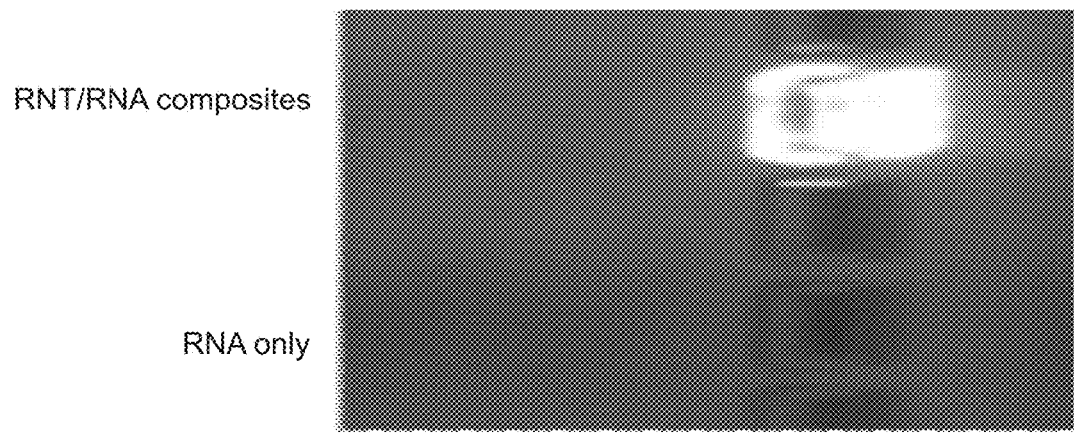
FIG. 5 are images of the electrophoresis of RNTs and RNT/RNA composites.

Electrophoresis was carried out to determine the incorporation of siRNAs into RNTs. 1 µL of 50 µM scrambled siRNA was incorporated with or without 5 µL of 1 mg/mL RNTs according to the method described above. 4% agarose gel was prepared for electrophoresis with ethidium bromide as fluorescence stain. Then, RNT/siRNA and RNT solution were mixed glycerol and the gel was run under 30V at 4° C. for 2 hours. Electrophoresis demonstrated the incorporation between RNTs and siRNAs and RNT/siRNA composites have a neutral total charge compared to negatively charged siRNA as shown in FIG. 5.

Figure 6:
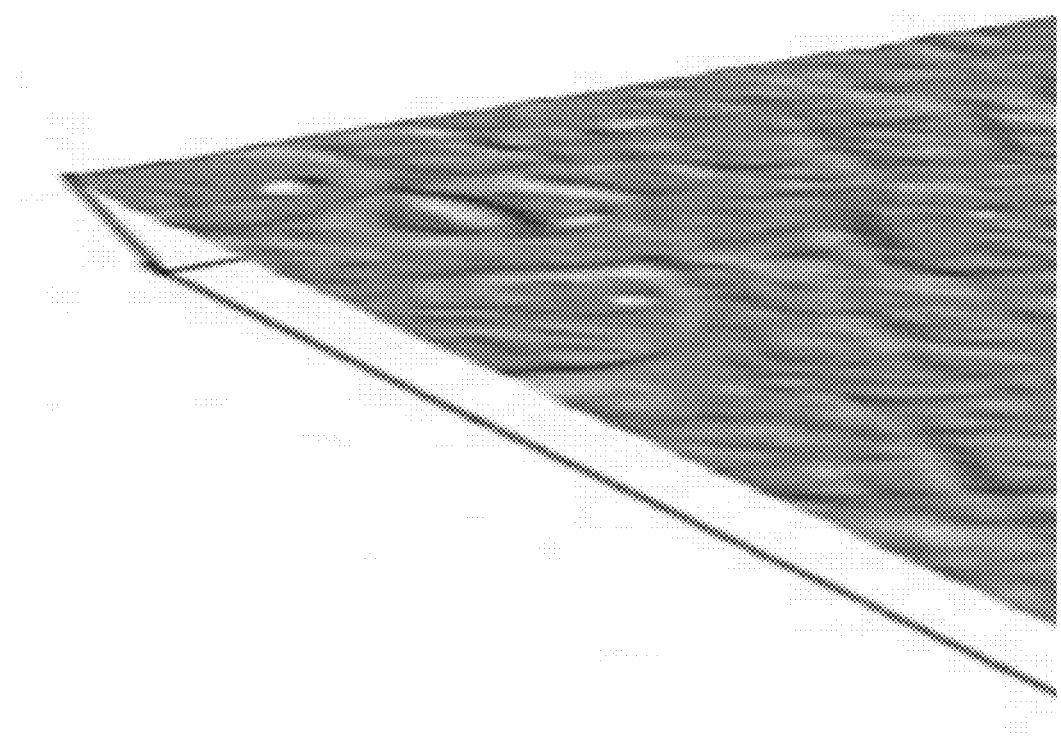
FIG. 6 is an atomic force microscopic image of rosette nanotubes only.
Figure 7B:
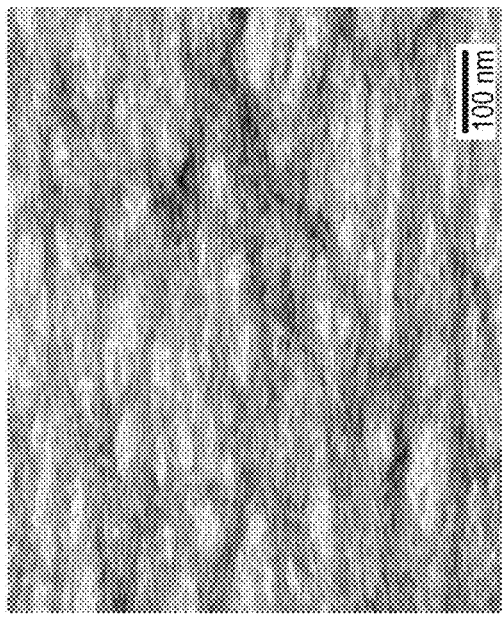
FIG. 7B is a transmission electron microscope image of RNTs.
Figure 7C:
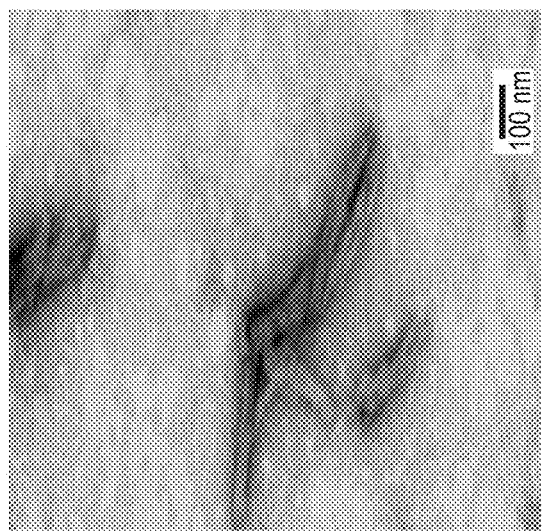
FIG. 7C is a transmission electron microscope image of a complex of RNTs and RNA.
Figure 7A:
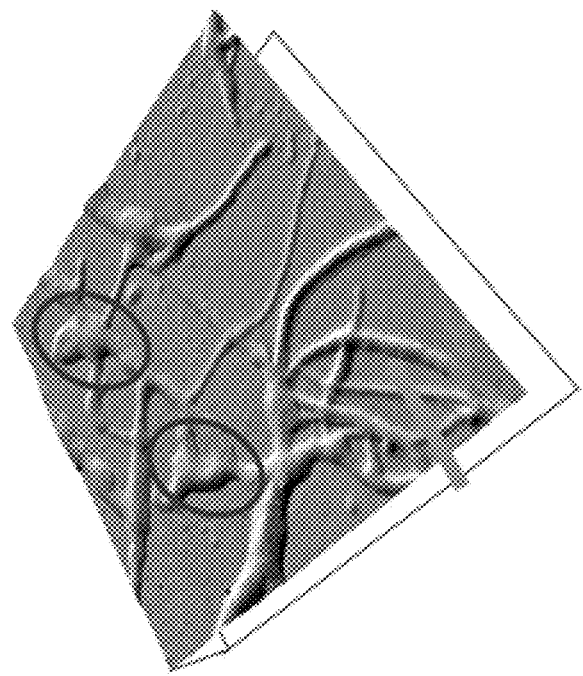
FIG. 7A is an atomic force microscopic image of a complex of rosette nanotubes and RNA.

Atomic force microscopic studies were carried out to analyze the surface of a network of RNTs and RNT/siRNA composites. RNT/siRNA composites were prepared as described above. 6 µl acetone was added to 10 µl of a solution of RNT/siRNA solution and a drop placed onto a clean glass slide. After air-drying, the glass slide was analyzed under atomic force microscopy. As shown in FIG. 6, RNTs formed a network morphology in a relatively high concentration. As shown in FIG. 7A, RNTs complexed with small RNAs showed regions of regions RNAs referred to as "clots" indicated by circles and "bundles" indicated by the arrow. Transmission electron microscopy was also used to analyze the morphologies of RNTs and RNT/siRNA composites. RNT/siRNA composites were prepared as described above. A copper grid was dip into RNT or RNT/siRNA solutions. After air-drying, the copper grid was negatively stained with uranyl acetate and analyzed under transmission electron microscopy. As shown in FIG. 7B, RNTs formed a network morphology. Consistent with atomic force microscopy, FIG. 7C shows that RNTs complexed with small RNAs and experienced a morphological transformation from net-work structures to particle-like structures.

Example 3

Chondrocytes Transfected with RNT/siRNA Complexes

Figure 8B:
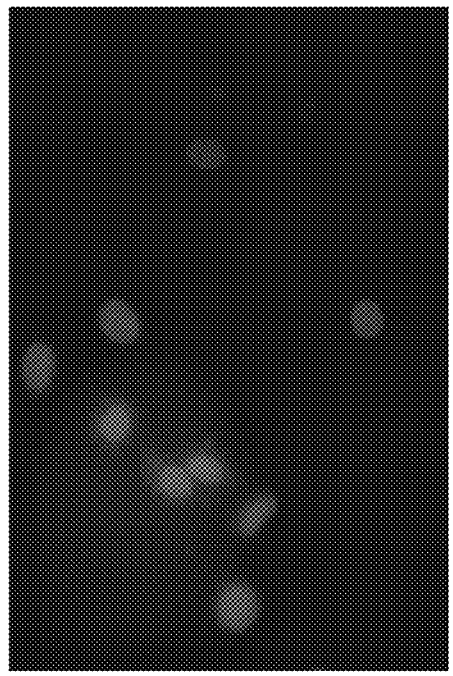
FIGS. 8A-8D are images of fluorescence microscopy of the treated cells revealing internalized RNT/SiRNA. Light (FIGS. 8A and 8C) and fluorescent (FIGS. 8B and 8D) pictures of chondrocytes cultured with only FITC-RNA (FIGS. 8A and 8B) or with FITC-RNA-RNTs (FIGS. 8C and 8D).
Figure 8D:
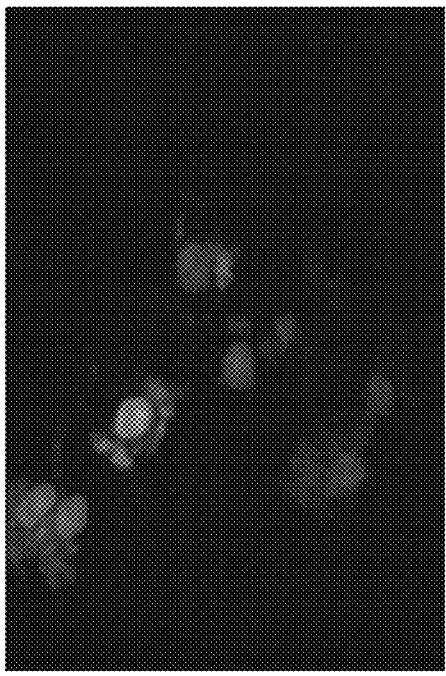
Figure 8A:
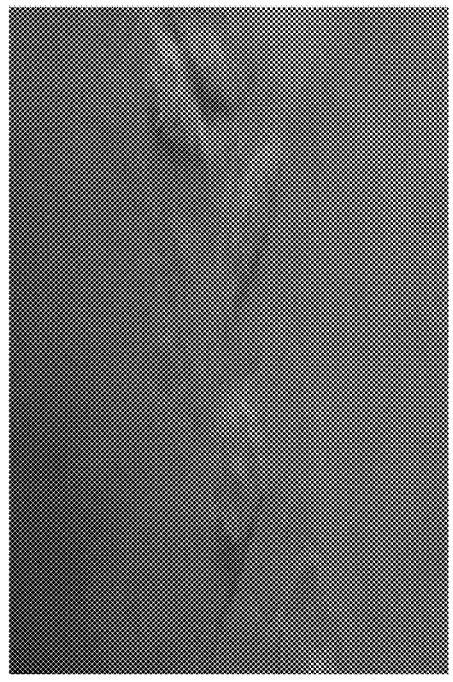
Figure 8C:
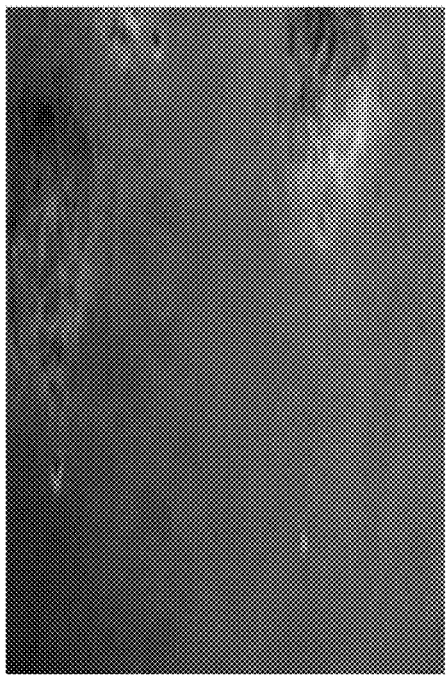

To visualize internalization of siRNA by RNT delivery into chondrocytes, RNTs/FITC-siRNA complex were added into ADTC5 mouse chondrocyte cell lines and incubated for 24 hours. The transfected cells were washed twice with PBS and then fixed in 4% formalin. Thereafter, cells were permeabilized with PBS/0.1% Triton X-100 and stained with HDAC4 antibody and incubated with DAPI for nuclear counterstaining. Confocal imaging was performed with a Zeiss Axiovert confocal laser scanning microscope. Fluorescence microscopy of the treated cells revealed internalized RNT/SiRNA. FIGS. 8A-8D depict light (8A and 8C) and fluorescent (8B and 8D) pictures of chondrocytes cultured with only FITC-RNA (8A and 8B) or with FITC-RNA-RNTs (8C and 8D). As shown in FIG. 8B, fluorescence labeled siRNA alone was not able to enter the cells. After incubation of fluorescent labeled siRNA with RNT as a carrier, the cells showed intracellular green fluorescent signals as shown in FIG. 8D. This demonstrates efficient uptake of RNT/RNA by chondrocytes.

Example 4

Primary Chondrocytes Transfected with RNT/siRNA Complexes

Figure 9E:
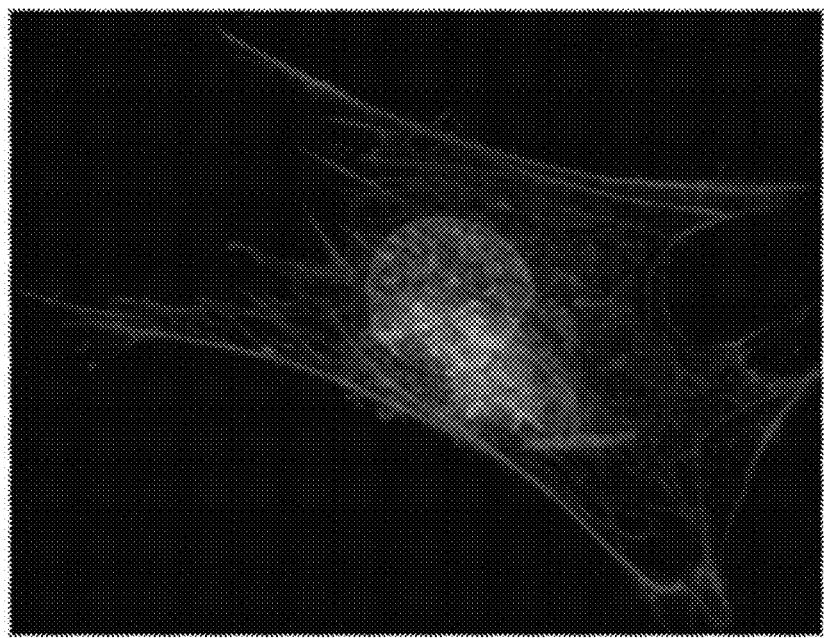
Figure 9F:
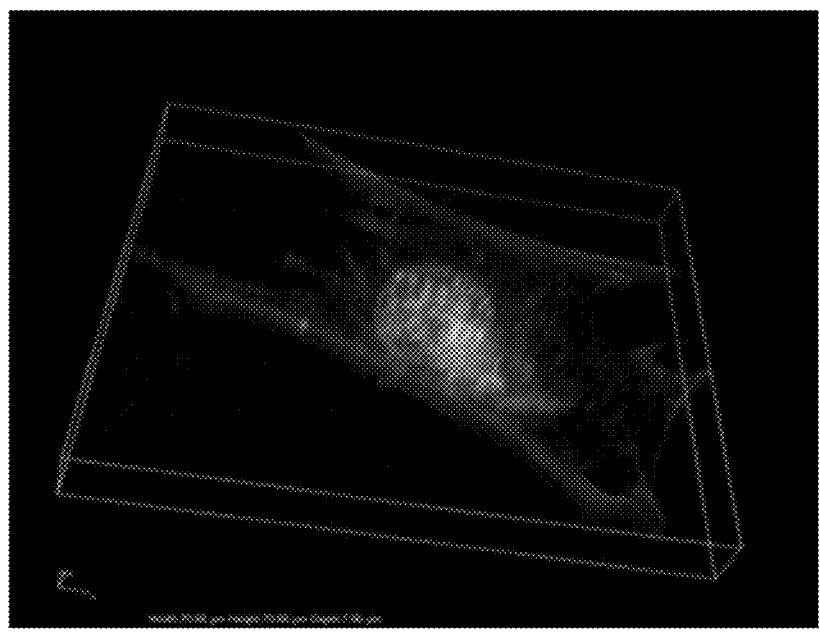

To test whether RNT can carry siRNA into primary chondrocytes, mouse primary chondrocytes were incubated with RNT/siRNA complex for 24 hours and observed by confocal microscophy. Briefly, the cells were washed twice with PBS and then fixed in 4% formalin. Thereafter, cells were permeabilized with PBS/0.1% Triton X-100 and stained with rhodamine and incubated with DAPI for nuclear counterstaining. The internalized HDAC4 siRNA accumulated in the cytoplasm and colocalized with HDAC4 protein as shown in FIGS. 9A-9F. In particular, FIGS. 9E and 9F are 2D and 3D images of green fluorescent siRNA delivered by RNTs inside a chondrocyte. Red fluorescence indicates the cytoskeleton and blue fluorescence indicates the cell nuclei.

Example 5

Inhibition of Protein Expression Using RNT/siRNA Complexes

Figure 10A:
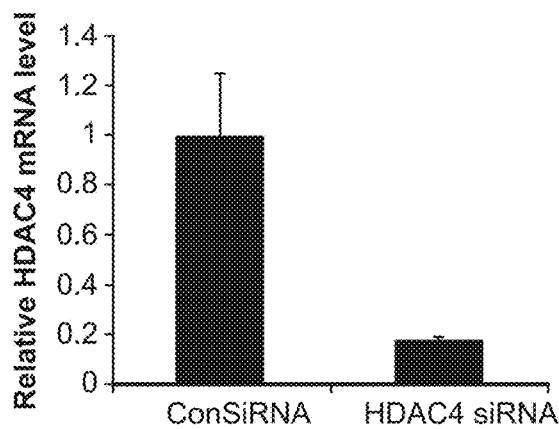
FIGS. 10A-10C depict images showing that siRNA delivered into chondrocytes by RNT induced the RNAi response. HDAC4 mRNA level was determined by the real-time PCR (FIG. 10A) and HDAC4 protein expression by western blot (FIG. 10B) and quantitative analysis of HDAC4 protein expression (FIG. 10C). *$P<0.05$ compared with the con-siRNA.
Figure 10B:
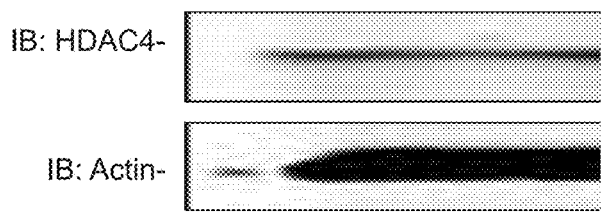
Figure 10C:
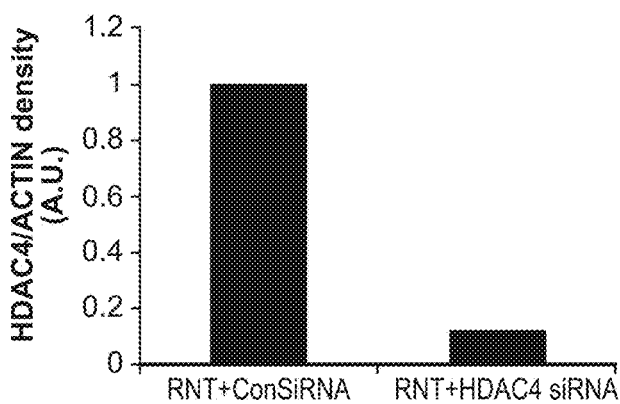

To evaluate the ability of RNT/siRNA complex to interfere with RNA in primary mouse chondrocytes, RNA was isolated and HDAC4 gene silencing was evaluated by real-time PCR. Chondrocytes were lyzed in RIPA lysis buffer and equal amount of cell lysates were separated by 10% SDS-PAGE and transferred on a nitrocellulose membrane. Membranes were blot with HDAC4 or Actin antibody Immunoblotting coupled with fluorescent signal detection with an Odyssey fluorescence scanner. As shown in FIG. 10A, expression level of HDAC4 mRNA was suppressed by nearly 80%. As shown in FIG. 10B, Western blot analysis indicated that HDAC4 protein expression was successfully inhibited. The efficient gene silencing indicates that siRNA delivered by RNT was functional in the cells. FIG. 10C depicts the quantitative analysis of the Western blots of FIG. 10B demonstrating that siRNAs were highly functional after delivery by RNTs into cells.

Example 6

Alteration of miRNA Expression Using RNT/miR365 Mimic or Inhibitor Complexes

Figure 11:
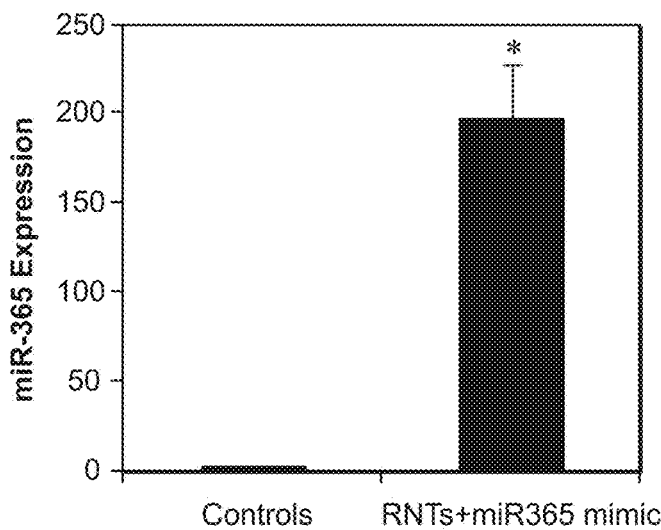
FIG. 11 is a graph demonstrating that miRNA was functionally delivered into chondrocytes by RNTs to induce RNAi response with an increase of miRNA 365 expression level. *$P<0.05$ compared with the controls.

To evaluate the ability of RNTs to deliver miRNA mimic into cells, RNT/miR365 mimic complexes were prepared using the methods described above. Human chondrocytes (C28I2) were contacted with the complexes and then the expression levels of miR365 were determined Briefly, total RNA was extracted from cells using a commercially available kit by following the manufacturer's instructions. Then, the RNA was reverse transcribed using the miscript reverse transcription kit and analyzed by real-time PCR using the appropriate miscript primer assay as per the manufacturer's instructions. For gene expression assay, the same amount of RNA was used for each sample. The 18 S RNA was amplified at the same time and used as an internal control. As shown in FIG. 11, the RNT/miR365 mimic complexes successfully delivered miR365 mimic into cells and the delivered miR365 mimic was functional to increase miR365 gene expression.

Figure 12A:
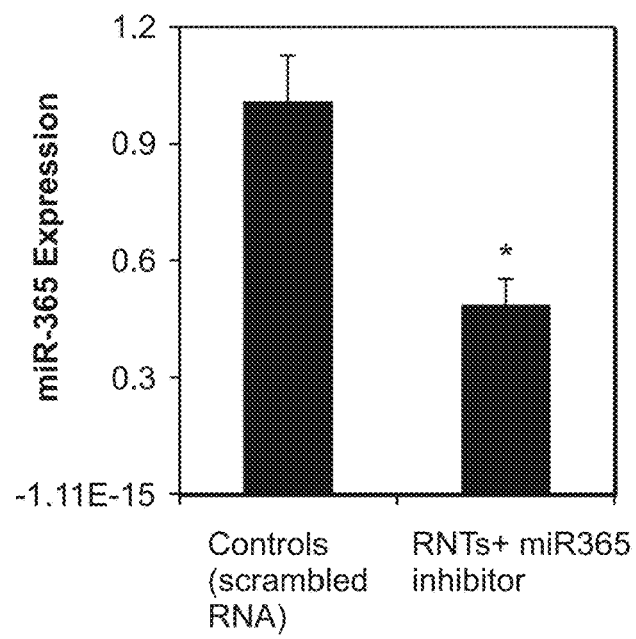
FIG. 12A is a graph demonstrating that miRNA inhibitor was functionally delivered into chondrocytes by RNTs to induce RNAi response with a decrease of miRNA 365 expression level.

To evaluate the ability of RNTs to deliver miRNA inhibitor into cells, RNT/miR365 inhibitor complexes were prepared using the methods described above. Human chondrocytes (C28I2) were contacted with the complexes and then the expression levels of miR365 were determined Briefly, total RNA was extracted from cells using a commercially available kit by following the manufacturer's instructions. Then, the RNA was reverse transcribed using the miscript reverse transcription kit and analyzed by real-time PCR using the appropriate miscript primer assay as per the manufacturer's instructions. For gene expression assay, the same amount of RNA was used for each sample. The 18 S RNA was amplified at the same time and used as an internal control. As shown in FIG. 12A, the RNT/miR365 inhibitor complexes successfully delivered miR365 inhibitor into the cells and the delivered miR365 inhibitor was functional to decrease miR365 gene expression.

Figure 12B:
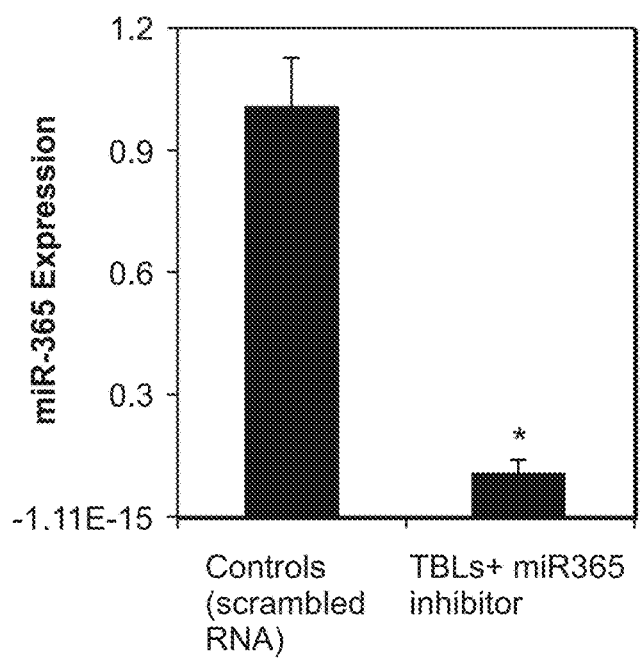
FIG. 12B a graph demonstrating that miRNA inhibitor was functionally delivered into chondrocytes by TBLs to induce RNAi response with a decrease of miRNA 365 expression level. *$P<0.05$ compared with the controls (scrambled RNA).

To evaluate the ability of RNTs such as TBLs to deliver miRNA inhibitor into cells, TBL/miR365 inhibitor complexes were prepared using the methods described above. Human chondrocytes (C28I2) were contacted with the complexes and then the expression levels of miR365 determined. Briefly, total RNA was extracted from cells using a commercially available kit by following the manufacturer's instructions. Then, the RNA was reverse transcribed using the miscript reverse transcription kit and analyzed by real-time PCR using the appropriate miscript primer assay as per the manufacturer's instructions. For gene expression assay, the same amount of RNA was used for each sample. The 18 S RNA was amplified at the same time and used as an internal control. As shown in FIG. 12B, the TBL/miR365 inhibitor complexes successfully delivered miR365 inhibitor into the cells and the delivered miR365 inhibitor was functional to decrease miR365 gene expression. As indicated in a comparison between FIG. 12A and FIG. 12B, the miR365 inhibitor delivered using rosette nanotubes made from the TBL decreased the miR365 expression to a greater extent than the miR365 inhibitor delivered using rosette nanotubes made from the RNT.

Example 7

Mouse Chondrocytes (ADTC5) Transfected with RNT/Probe Complexes

Figure 13B:
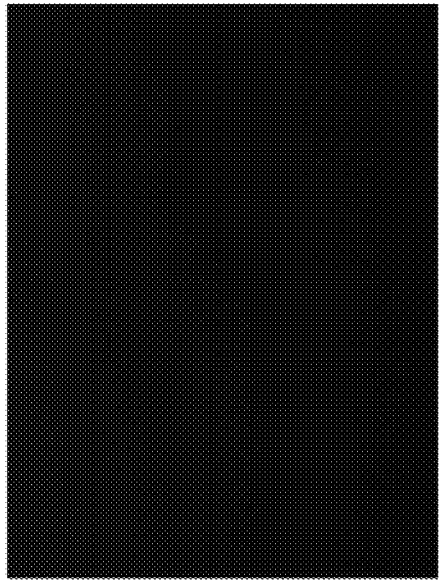
FIGS. 13A-13D depict images of internalized RNT/GAPDH molecular beacons located in the cytoplasm. Light (FIG. 13A and FIG. 13C) and fluorescent (FIG. 13B and FIG. 13D) pictures of ADTC5 chondrocytes cultured with only GAPDH molecular beacons (A and B) or with RNT/GAPDH molecular beacons (FIG. 13C and FIG. 13D).
Figure 13D:
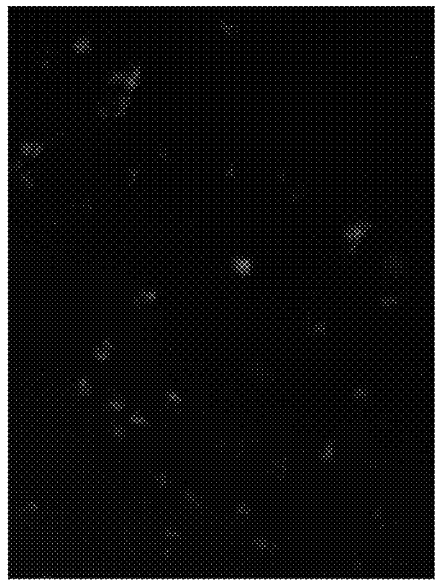
Figure 13A:
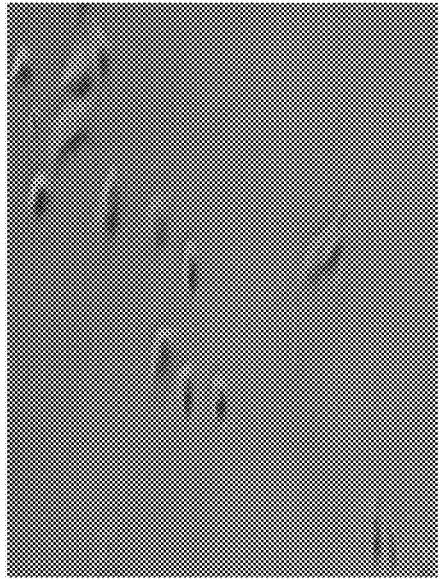
Figure 13C:
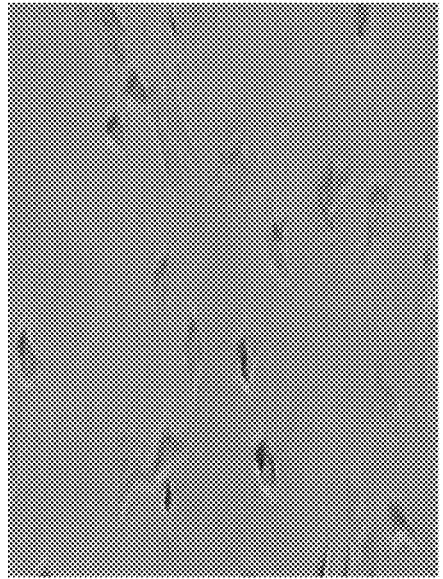

To test whether RNT can carry a nucleic acid probe, such as a molecular beacon capable of hybridizing with or otherwise binding to a target gene, RNT/molecular beacon complexes were prepared using the methods described above. Mouse chondrocytes (ADTC5) were incubated with RNT/GAPDH molecular beacon targeting GAPDH expression complex for 24 hours and observed by confocal microscopy. Briefly, the cells were washed twice with PBS and then fixed in 4% formalin for confocal microscopy. FIG. 13 depicts light (13A and 13C) and fluorescent (13B and 13D) pictures of chondrocytes cultured with only the GAPDH molecular beacon (13A and 13B) or with RNT/GAPDH molecular beacon complex (13C and 13D). As shown in FIG. 13B, fluorescence labeled GAPDH molecular beacon alone was not able to enter the cells. After incubation of fluorescent labeled GAPDH molecular beacon with RNT as a carrier, cells showed intracellular green fluorescent signals as shown in FIG. 13D. This demonstrates efficient uptake of RNT/GAPDH molecular beacon complexes by mouse chondrocytes.

Example 8

Chicken Primary Chondrocytes Transfected with RNT/Probe Complexes

Figure 14B:
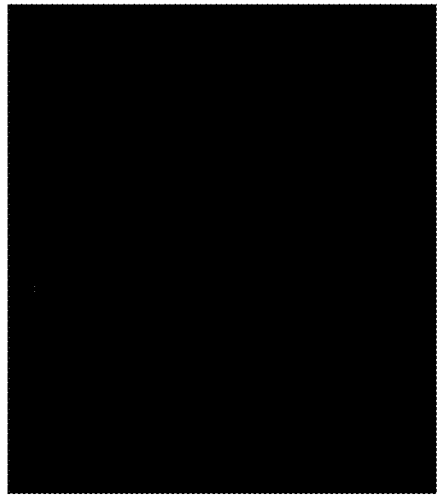
FIGS. 14A-14D depict images of internalized RNT/GAPDH molecular beacons located in the cytoplasm. Light (FIG. 14A and FIG. 14C) and fluorescent (FIG. 14B and FIG. 14D) pictures of primary chicken chondrocytes cultured with only GAPDH molecular beacons (FIG. 14A and FIG. 14B) or with RNT/GAPDH molecular beacons (FIG. 14C and FIG. 14D).
Figure 14D:
Figure 14A:
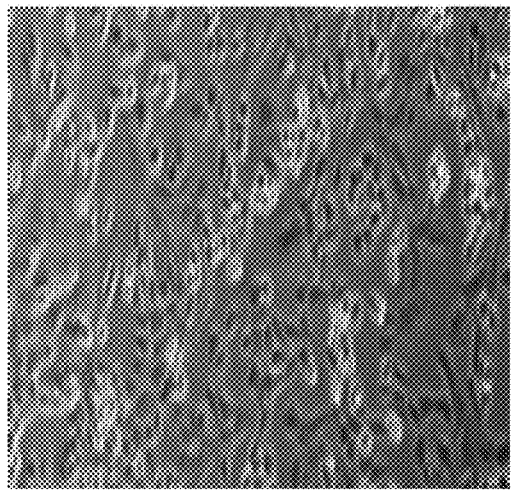
Figure 14C:
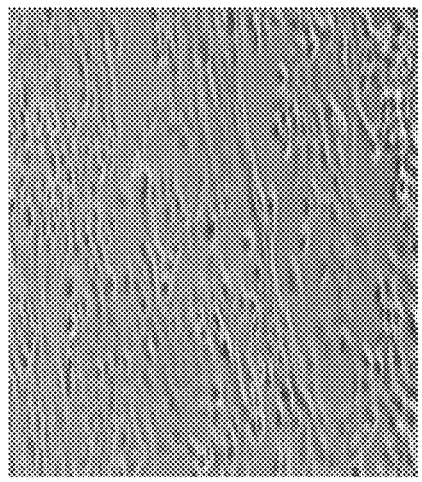
Figure 17B:
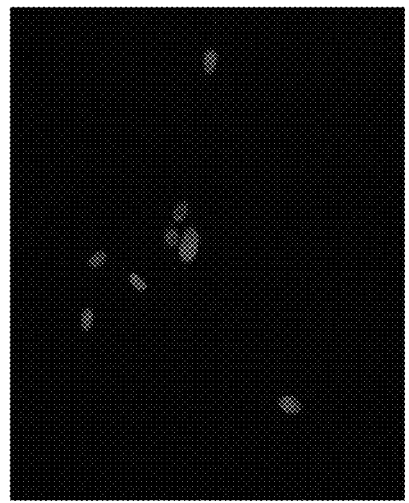
FIGS. 17A-17D depict images of internalized RNT/green fluorescence labeled siRNA located in the cytoplasm. Light (FIG. 17A and FIG. 17C) and fluorescent (FIG. 17B and FIG. 17D) pictures of primary pig chondrocytes cultured with only siRNA (FIG. 17A and FIG. 17B) or with RNT/siRNA (FIG. 17C and FIG. 17D).
Figure 17D:
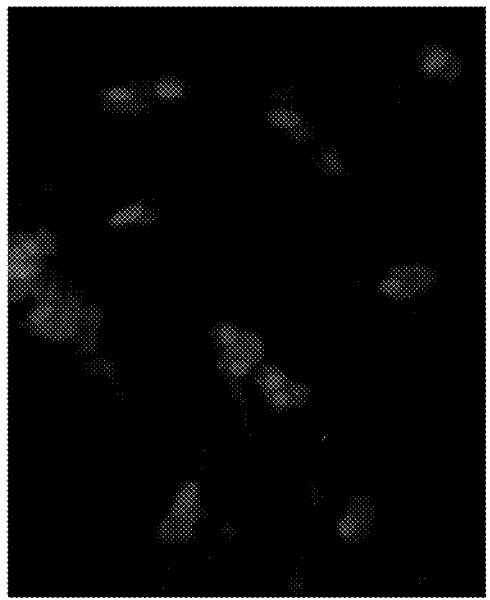
Figure 17A:
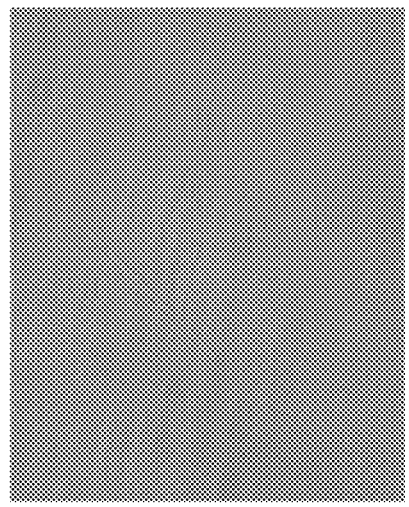
Figure 17C:
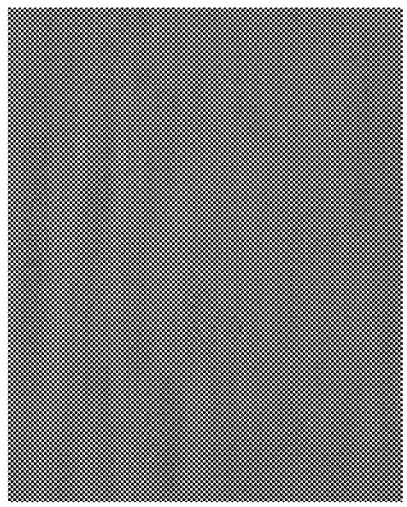
Figure 19B:
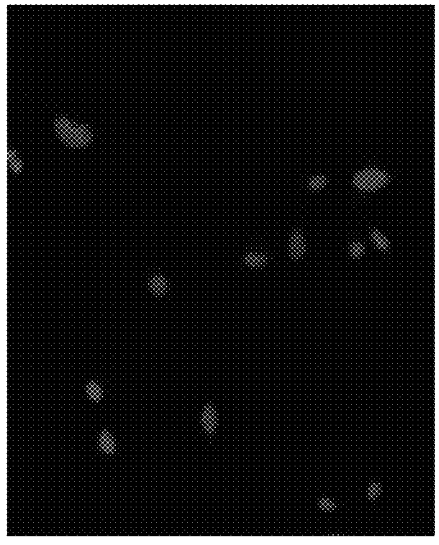
FIGS. 19A-19D depict images of internalized RNT/green fluorescence labeled siRNA located in the cytoplasm. Light (FIG. 19A and FIG. 19C) and fluorescent (FIG. 19B and FIG. 19D) pictures of rat astrocyte cell line (CRL2005) cultured with only siRNA (FIG. 19A and FIG. 19B) or with RNT/siRNA (FIG. 19C and FIG. 19D).
Figure 19D:
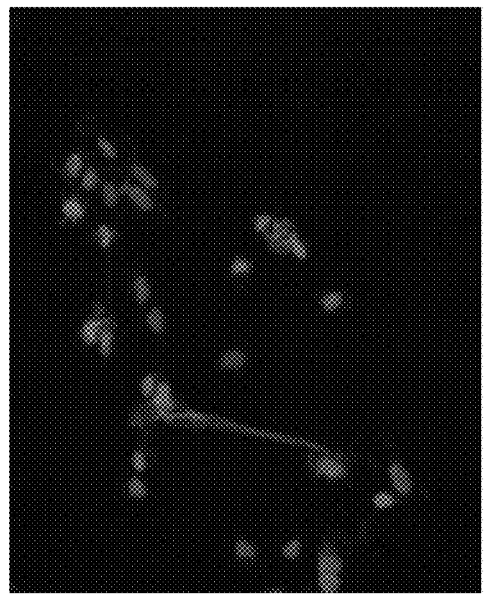
Figure 19A:
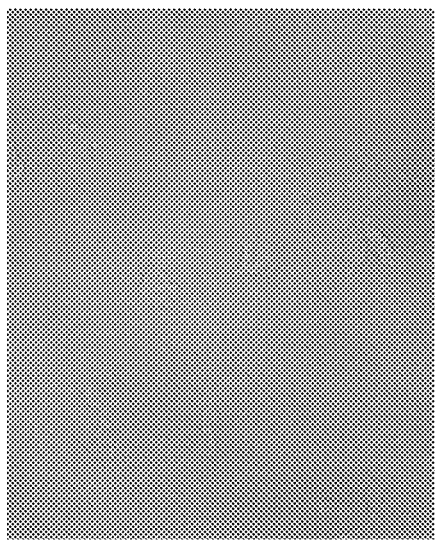
Figure 19C:
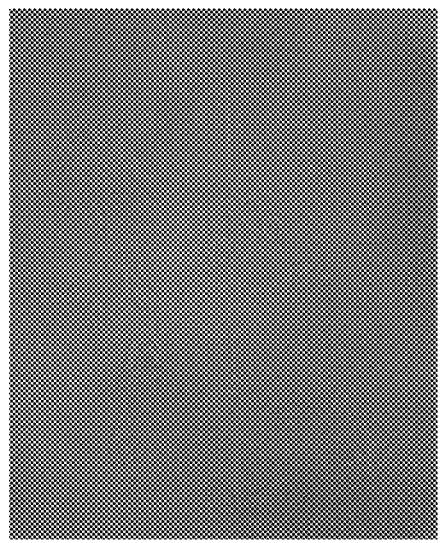
Figure 20B:
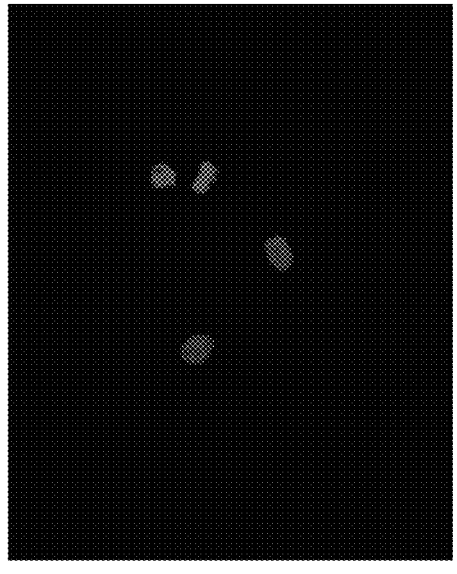
FIGS. 20A-20D depict images of internalized RNT/green fluorescence labeled siRNA located in the cytoplasm. Light (FIG. 20A and FIG. 20C) and fluorescent (FIG. 20B and FIG. 20D) pictures of human chondrosarcoma cells cultured with only siRNA (FIG. 20A and FIG. 20B) or with RNT/siRNA (FIG. 20C and FIG. 20D).
Figure 20D:
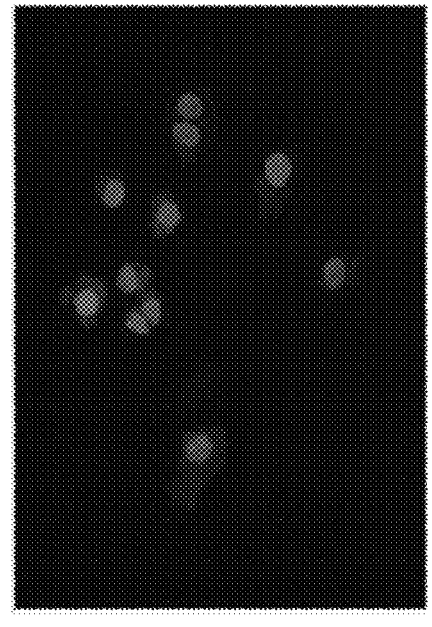
Figure 20A:
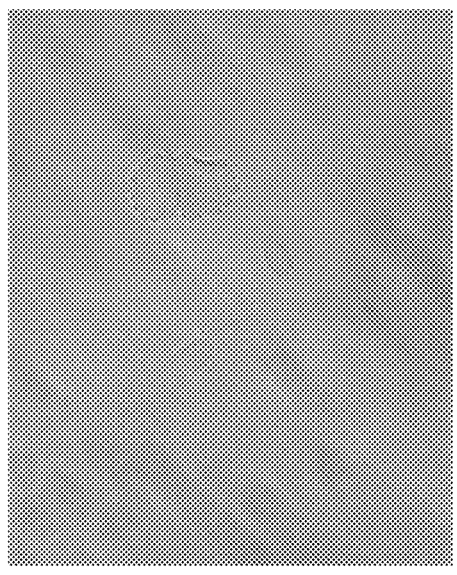
Figure 20C:
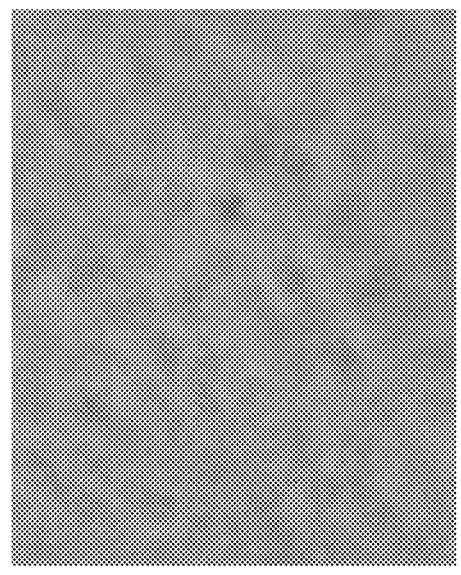
Figure 21B:
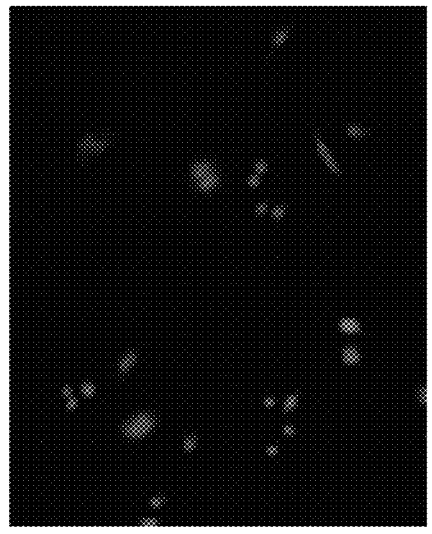
FIGS. 21A-21D depict images of internalized RNT/green fluorescence labeled siRNA located in the cytoplasm. Light (FIG. 21A and FIG. 21C) and fluorescent (FIG. 21B and FIG. 21D) pictures of mouse macrophage cell line (RAW 264.7) cultured with only siRNA (FIG. 21A and FIG. 21B) or with RNT/siRNA (FIG. 21C and FIG. 21D).
Figure 21D:
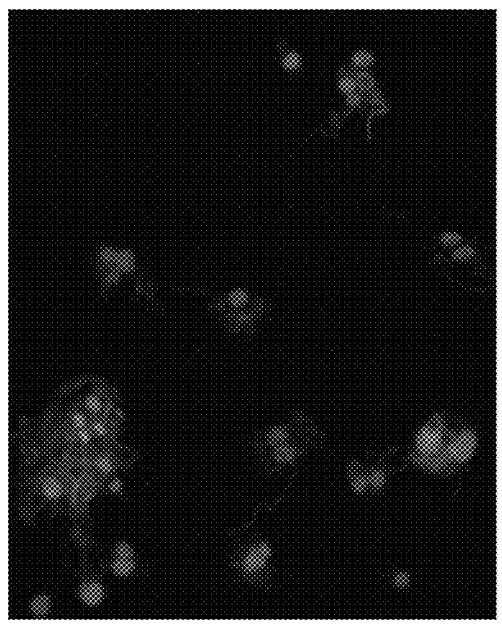
Figure 21A:
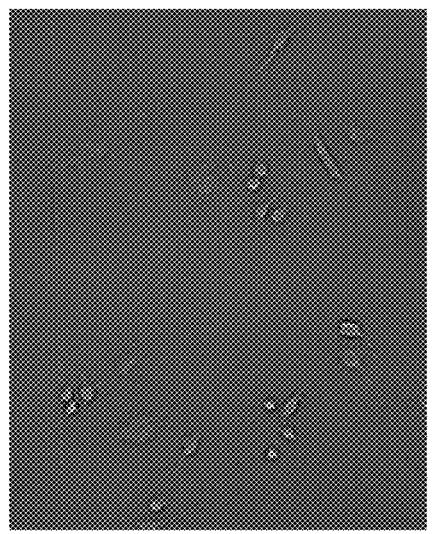
Figure 21C:
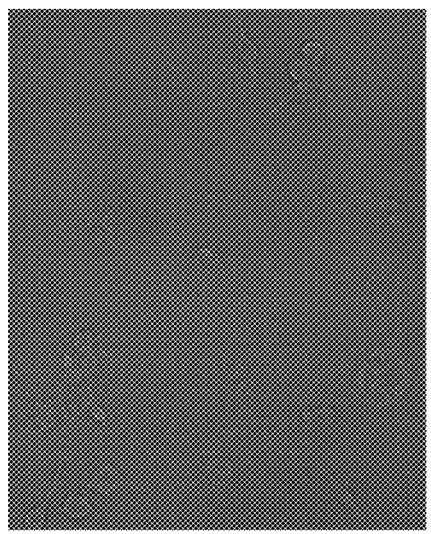
Figure 22B:
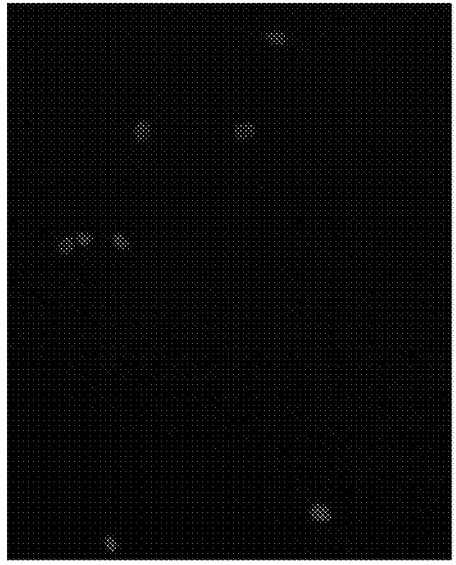
FIGS. 22A-22D depict images of internalized RNT/green fluorescence labeled siRNA located in the cytoplasm. Light (FIG. 22A and FIG. 22C) and fluorescent (FIG. 22B and FIG. 22D) pictures of primary chicken liver cells cultured with only siRNA (FIG. 22A and FIG. 22B) or with RNT/siRNA (FIG. 22C and FIG. 22D).
Figure 22D:
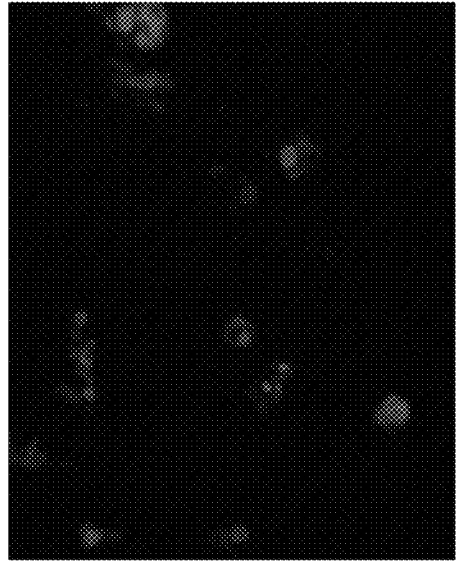
Figure 22A:
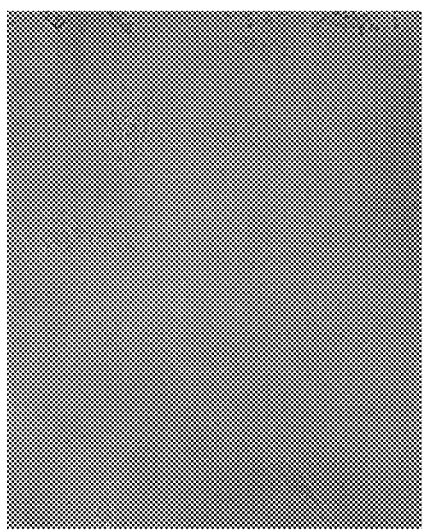
Figure 22C:
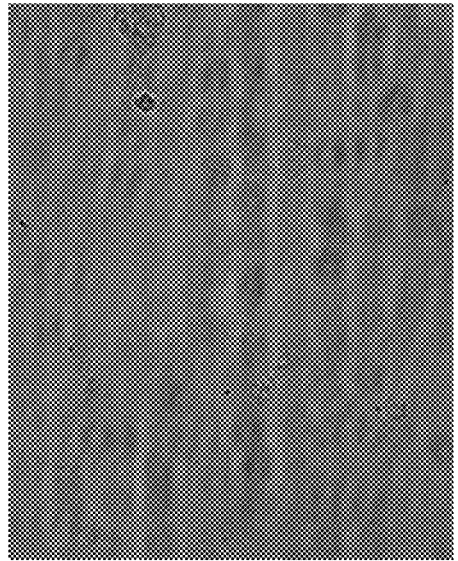

To test whether RNT can carry a nucleic acid probe, such as a molecular beacon capable of hybridizing with or otherwise binding to a target gene, RNT/molecular beacon complexes were prepared using the methods described above. Chicken primary chondrocytes were incubated with RNT/GAPDH molecular beacon targeting GAPDH expression complex for 24 hours and observed by confocal microscopy. Briefly, the cells were washed twice with PBS and then fixed in 4% formalin for confocal microscopy. FIG. 14 depicts light (14A and 14C) and fluorescent (14B and 14D) pictures of chondrocytes cultured with only GAPDH molecular beacon (14A and 14B) or with RNT/GAPDH molecular beacon complex (14C and 14D). As shown in FIG. 14B, fluorescence labeled GAPDH molecular beacon alone was not able to enter the cells. After incubation of fluorescent labeled GAPDH molecular beacon with RNT as a carrier, cells showed intracellular green fluorescent signals as shown in FIG. 14D. This demonstrates efficient uptake of RNT/GAPDH molecular beacon complexes by chicken chondrocytes.

Example 9

Mouse Chondrocytes Transfected with RNT/Probe Complexes

To test whether RNT can carry a nucleic acid probe, such as a molecular beacon capable of hybridizing with or otherwise binding to a target gene, RNT/molecular beacon complexes were prepared using the methods described above. Primary mouse chondrocytes were incubated with RNT/miR365 molecular beacon targeting miR365 expression complex for 24 hours and observed by confocal microscopy. Briefly, the cells were washed twice with PBS and then fixed in 4% formalin for confocal microscopy. FIG. 15 depicts light (15A and 15C) and fluorescent (15B and 15D) pictures of chondrocytes cultured with only miR365 molecular beacon (15A and 15B) or with RNT/miR365 molecular beacon complex (15C and 15D). As shown in FIG. 15B, fluorescence labeled miR365 molecular beacon alone was not able to enter the cells. After incubation of fluorescent labeled miR365 molecular beacon with RNT as a carrier, cells showed intracellular green fluorescent signals as shown in FIG. 15D. This demonstrates efficient uptake of RNT/miR365 molecular beacon complexes by mouse chondrocytes.

Example 10

Additional Cells Transfected with RNT/Probe Complexes

To test whether RNT can carry a nucleic acid into various cells, RNT/FITC-siRNA complexes were prepared using the methods described above. The RNT/FITC-siRNA complexes were separately incubated for 24 hours with primary human fibroblasts, primary pig fibroblasts, human breast cancer cell line MCF7, rat astrocyte cell line CRL2005, human chondrosarcoma cells, mouse macrophage cell line RAW 264.7, and primary chicken liver cells. The transfected cells were washed, fixed and stained as previously described. Fluorescence microscopy of the treated cells revealed internalized RNT/siRNA.

FIG. 16 depicts light (16A and 16C) and fluorescent (16B and 16D) pictures of primary human fibroblasts cultured with only FITC-siRNA (16A and 16B) or with RNT/FITC-siRNA complex (16C and 16D). As shown in FIG. 16B, FITC-siRNA alone was not able to enter the cells. After incubation of FITC-siRNA with RNT as a carrier, cells showed intracellular green fluorescent signals as shown in FIG. 16D. This demonstrates efficient uptake of RNT/FITC-siRNA complexes by primary human fibroblasts.

FIG. 17 depicts light (17A and 17C) and fluorescent (17B and 17D) pictures of primary pig fibroblasts cultured with only FITC-siRNA (17A and 17B) or with RNT/FITC-siRNA complex (17C and 17D). As shown in FIG. 17B, FITC-siRNA alone was not able to enter the cells. After incubation of FITC-siRNA with RNT as a carrier, cells showed intracellular green fluorescent signals as shown in FIG. 16D. This demonstrates efficient uptake of RNT/FITC-siRNA complexes by primary pig fibroblasts.

FIG. 18 depicts light (18A and 18C) and fluorescent (18B and 18D) pictures of human breast cancer cell line MCF7 cultured with only FITC-siRNA (18A and 18B) or with RNT/FITC-siRNA complex (18C and 18D). As shown in FIG. 18B, FITC-siRNA alone was not able to enter the cells. After incubation of FITC-siRNA with RNT as a carrier, cells showed intracellular green fluorescent signals as shown in FIG. 18D. This demonstrates efficient uptake of RNT/FITC-siRNA complexes by human breast cancer cell line MCF7.

FIG. 19 depicts light (19A and 19C) and fluorescent (19B and 19D) pictures of rat astrocyte cell line CRL2005 cultured with only FITC-siRNA (19A and 19B) or with RNT/FITC-siRNA complex (19C and 19D). As shown in FIG. 19B, FITC-siRNA alone was not able to enter the cells. After incubation of FITC-siRNA with RNT as a carrier, cells showed intracellular green fluorescent signals as shown in FIG. 19D. This demonstrates efficient uptake of RNT/FITC-siRNA complexes by rat astrocyte cell line CRL2005.

FIG. 20 depicts light (20A and 20C) and fluorescent (20B and 20D) pictures of human chondrosarcoma cells cultured with only FITC-siRNA (20A and 20B) or with RNT/FITC-siRNA complex (20C and 20D). As shown in FIG. 20B, FITC-siRNA alone was not able to enter the cells. After incubation of FITC-siRNA with RNT as a carrier, cells showed intracellular green fluorescent signals as shown in FIG. 20D. This demonstrates efficient uptake of RNT/FITC-siRNA complexes by human chondrosarcoma cells.

FIG. 21 depicts light (21A and 21C) and fluorescent (21B and 21D) pictures of mouse macrophage cell line RAW 264.7 cultured with only FITC-siRNA (21A and 21B) or with RNT/FITC-siRNA complex (21C and 21D). As shown in FIG. 21B, FITC-siRNA alone was not able to enter the cells. After incubation of FITC-siRNA with RNT as a carrier, cells showed intracellular green fluorescent signals as shown in FIG. 21D. This demonstrates efficient uptake of RNT/FITC-siRNA complexes by mouse macrophage cell line RAW 264.7.

FIG. 22 depicts light (22A and 22C) and fluorescent (22B and 22D) pictures of primary chicken liver cells cultured with only FITC-siRNA (22A and 22B) or with RNT/FITC-siRNA complex (22C and 22D). As shown in FIG. 22B, FITC-siRNA alone was not able to enter the cells. After incubation of FITC-siRNA with RNT as a carrier, cells showed intracellular green fluorescent signals as shown in FIG. 22D. This demonstrates efficient uptake of RNT/FITC-siRNA complexes by primary chicken liver cells.

Example 11

In Vivo Delivery of RNT/Probe Complexes to Cells

Figure 23:
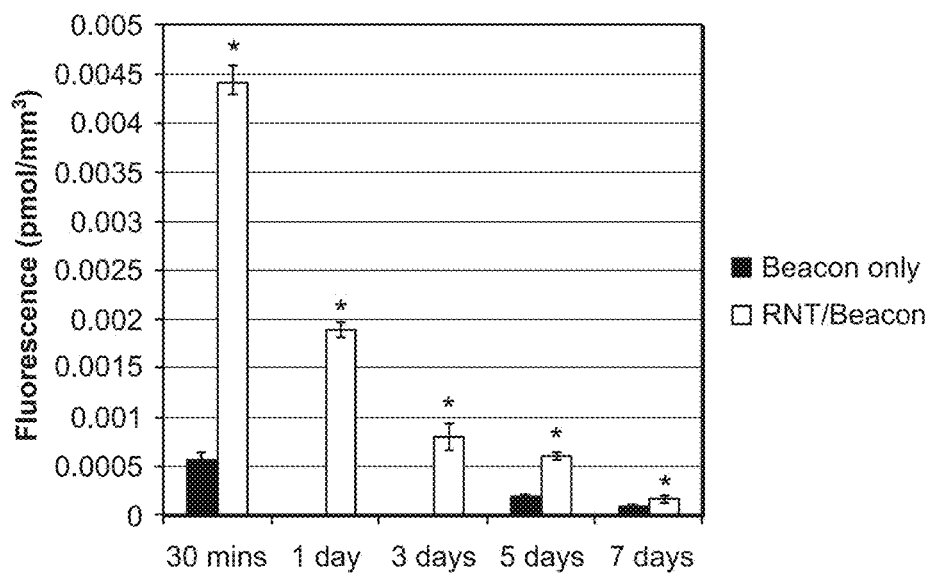
FIG. 23 is the quantitative analysis of the fluorescence molecular tomography in the mouse. *$P<0.05$ compared with the control group (Beacon only) at the respective time point.

To test whether RNT can carry nucleic acids to cells in an animal in vivo, RNT/GAPDH molecular beacon targeting GAPDH expression was prepared using the methods described above. The right femur of a 3 month old male mouse was injected with the GAPDH molecular beacon in a 30 µl saline solution. The left femur of a 3 month old male mouse was injected with the RNT/GAPDH molecular beacon complex in a 30 µl saline solution. After injection, fluorescence molecular tomography was used to measure the fluorescence of the molecular beacons at 30 minutes, 1 day, 3 days, 5 days and 7 days. FIG. 23 shows a significantly higher fluorescence signal from the left femur which was injected with the RNT/molecular beacon complex compared to the right femur which was injected with the molecular beacon only. This demonstrates that the RNTs were able to deliver the molecular beacons into cells in vivo.

Example 12

Comparison with Lipofectamine

Figures 24A, 24B, 24C:
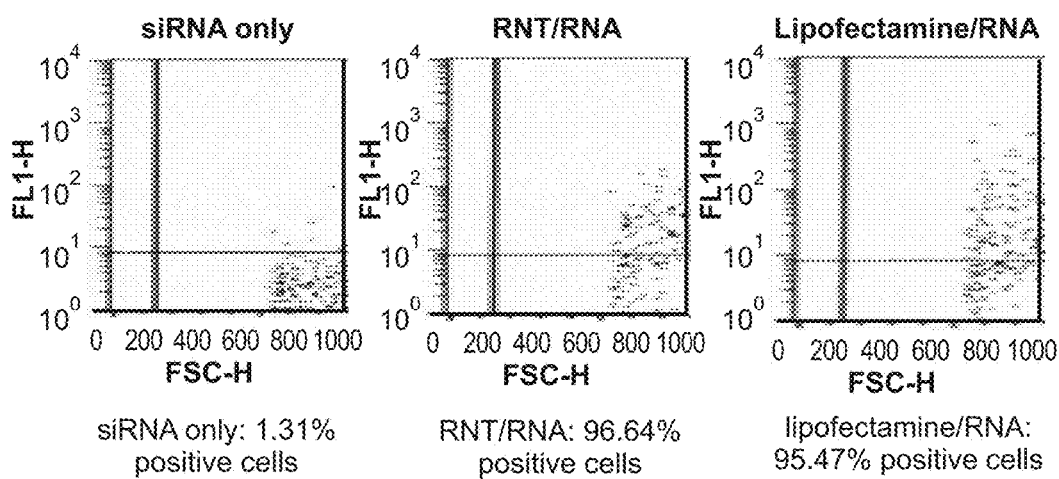
FIG. 24 is flow cytometry data showing the fluorescence of cells cultured with siRNA only, RNT/RNA and Lipofectamine/RNA.
Figure 25:
FIGS. 25A-25D are graphs comparing the ability of lipofectamine and RNTs to deliver GAPDH molecular beacons into cells. Light (FIG. 25A and FIG. 25C) and fluorescent (FIG. 25B and FIG. 25D) pictures of primary mouse chondrocytes cultured with lipofectamine/GAPDH molecular beacons (FIG. 25A and FIG. 25B) or with RNT/GAPDH molecular beacons (FIG. 25C and FIG. 25D).
Figure 25D:
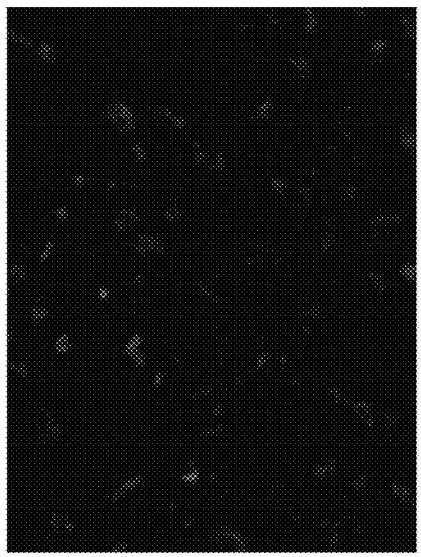
Figure 25A:
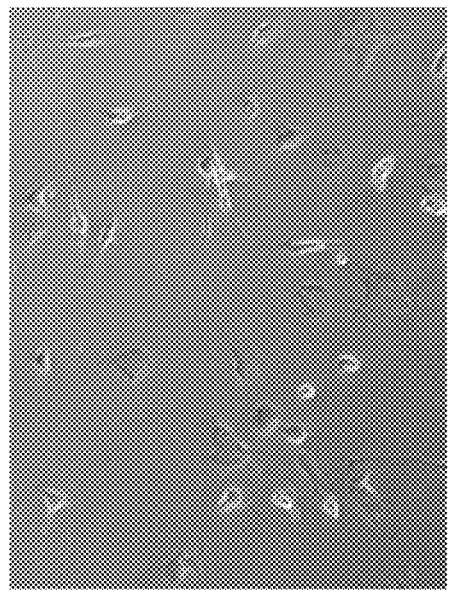
Figure 25C:
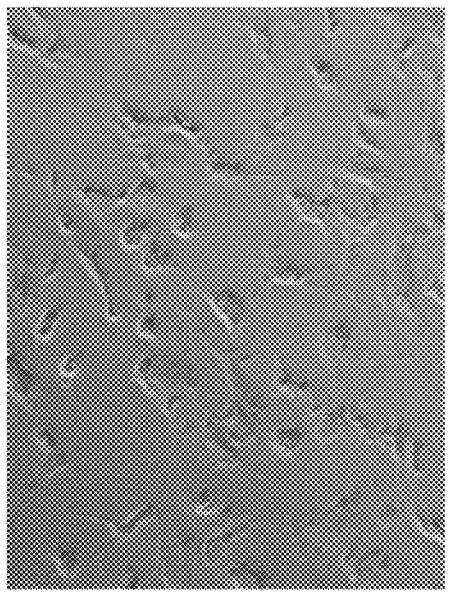

The ability of RNTs to deliver siRNA was compared with that of lipofectamine. Briefly, RNT/fluorescence labeled siRNA were prepared using the methods mentioned above and Lipofectamine/fluorescence labeled siRNA complexes were prepared as per the standard commercially available protocol. Mouse chondrocytes (ADTC5) were incubated with RNA only, RNT/RNA and Lipofectamine/RNA for 24 hours. Then, the cells were washed with PBS, detached from the culture dishes and fixed by 4% formalin. Flow cytometry was used to determine the percentage of fluorescent cells. Fluorescence positive cells demonstrated the uptake of siRNA. Results demonstrated that RNTs deliver siRNA into cells while siRNA alone was not capable of entering cells. Flow cytometry data as depicted in FIGS. 24A-24C show that delivery of siRNA into cells was as good as or better than lipofectamine. Especially, RNTs showed a more even distribution of fluorescence among cells.

To compare the ability of RNT and lipofectamine to deliver a GAPDH molecular beacon, RNT/GAPDH molecular beacon complexes were prepared using methods described above and Lipofectamine/GAPDH molecular beacon complexes were prepared as per the standard commercially available protocol. Primary mouse chondrocytes were incubated with GAPDH molecular beacon, RNT/GAPDH molecular beacon complexes, and Lipofectamine/GAPDH molecular beacon complexes for 24 hours and observed by confocal microscopy. As shown in FIGS. 25A-25D, RNTs demonstrated a significantly better delivery ability to deliver molecular beacons into chondrocytes that lipofectamine at the same dose.

Example 13

Downstream Gene Expression Comparison with Lipofectamine

Figure 26:
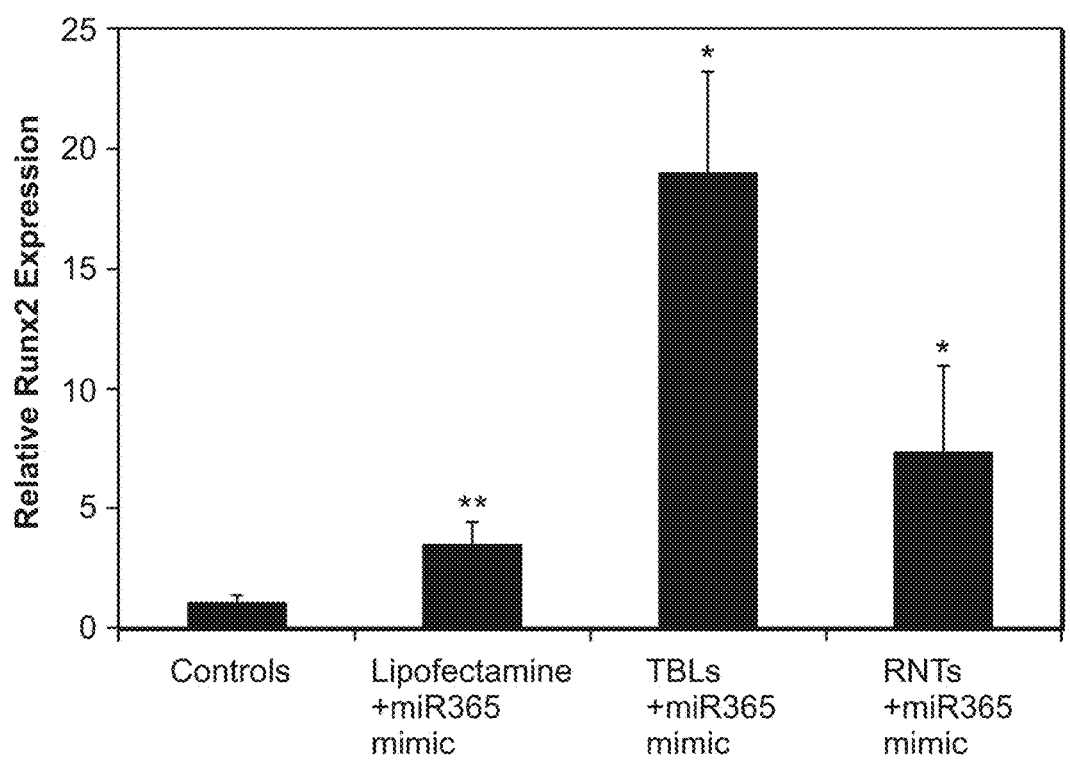
FIG. 26 a graph comparing the ability of lipofectamine, TBLs and RNTs to deliver miR365 mimic into cells and to influence expression of downstream gene. *P<0.05 compared with the controls and lipofectamine/miR365 mimic. **P<0.05 compared with the controls.

The ability of RNTs, TBLs and lipofectamine to deliver miR365 mimic into human chondrocytes (C28I2) and to influence expression of the downstream gene RUNX2 was determined. Briefly, total RNA was extracted from cells using a commercially available kit by following the manufacturer's instructions. Then, the RNA was reverse transcribed using the miscript reverse transcription kit and analyzed by real-time PCR using the appropriate miscript primer assay as per the manufacturer's instructions. For gene expression assay, the same amount of RNA was used for each sample. The 18 S RNA was amplified at the same time and used as an internal control. RNT/miR365 mimic and TBL/miR365 mimic complexes were prepared using the methods described herein and lipofectamine/miR365 mimic was prepared as the standard commercially available protocol. As shown in FIG. 26, delivery of miR365 mimic into cells using RNTs and TBLs increased expression of the downstream gene RUNX2 and to a greater extent compared with lipofectamine.

Given the benefit of the above disclosure and description of exemplary embodiments, it will be apparent to those skilled in the art that numerous alternative and different embodiments are possible in keeping with the general principles of the invention disclosed here. Those skilled in this art will recognize that all such various modifications and alternative embodiments are within the true scope and spirit of the invention. While the invention has been illustrated and described in detail in the drawings and foregoing description, such illustration and description is to be considered as exemplary and not restrictive in character, it being understood that, only the preferred embodiments have been shown and described and that all changes and modifications that come within the spirit of the invention are desired to be protected. The appended claims are intended to cover all such modifications and alternative embodiments. It should be understood that the use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc. References identified herein are expressly incorporated herein by reference in their entireties unless otherwise indicated.

What is claimed is:

1. A method of delivering one or more nucleic acids into a cell comprising contacting the cell with a complex of the one or more nucleic acids and a structure formed from the assembly of one or more compounds in aqueous media having the formula

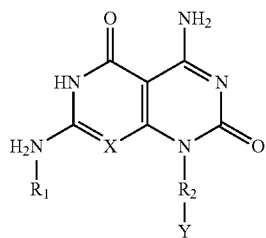

wherein X is CH or nitrogen; $R_2$ is hydrogen or a linker group; Y is absent when $R_2$ is hydrogen or is an amino acid or polypeptide having an amino group covalently bound to an α-carbon of the amino acid and the amino group is covalently bound to the linker group $R_2$; and $R_1$ is hydrogen or an aliphatic moiety; and salts thereof in a manner to deliver the complex into the cell.

2. A complex comprising one or more nucleic acids and a structure formed from the assembly of compounds having the formula

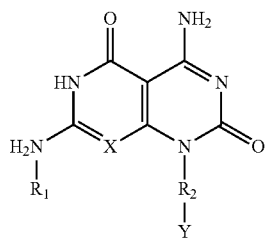

wherein X is CH or nitrogen; $R_2$ is hydrogen or a linker group; Y is absent when $R_2$ is hydrogen or is an amino acid or polypeptide having an amino group covalently bound to an α-carbon of the amino acid and the amino group is covalently bound to the linker group $R_2$; and $R_1$ is hydrogen or an aliphatic moiety; and salts thereof.

3. The method of claim 1 wherein the aliphatic moiety is a straight chain or a branched alkyl group being saturated or unsaturated.

4. The complex of claim 2 wherein the aliphatic moiety is a straight chain or a branched alkyl group being saturated or unsaturated.

5. The method of claim 1 wherein $R_2$ is the linker group $(CH_2)_n$ where n is 1, 2, 3 or 4 and Y is lysine.

6. A method of delivering one or more nucleic acids into a cell comprising contacting the cell with a complex of the one or more nucleic acids and a structure formed from the assembly of one or more compounds in aqueous media having the formula

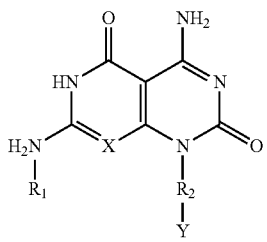

wherein X is CH or nitrogen; $R_2$ is hydrogen or a linker group; Y is absent when $R_2$ is hydrogen or is an amino acid or polypeptide having an amino group covalently bound to an a-carbon of the amino acid and the amino group is covalently bound to the linker group $R_2$; and $R_1$ is hydrogen or an aliphatic moiety; and salts thereof in a manner to deliver the complex into the cell, wherein the one or more nucleic acids include DNA, RNA, a gene, a gene fragment, an exon, an intron, intergenic DNA, heterochromatic DNA, messenger RNA, transfer RNA, interference RNA, dsRNA, ssRNA, saRNA, siRNA, miRNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, a molecular beacon or a primer.

7. A method of delivering one or more nucleic acids into a cell comprising contacting the cell with a complex of the one or more nucleic acids and a structure formed from the assembly of one or more compounds in aqueous media having the formula

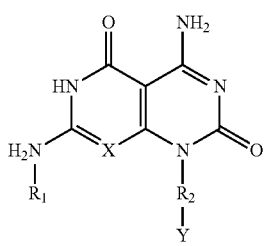

wherein X is CH or nitrogen; $R_2$ is hydrogen or a linker group; Y is absent when $R_2$ is hydrogen or is an amino acid or polypeptide having an amino group covalently bound to an α-carbon of the amino acid and the amino group is covalently bound to the linker group $R_2$; and $R_1$ is hydrogen or an aliphatic moiety; and salts thereof in a manner to deliver the complex into the cell, wherein the one or more nucleic acids includes siRNA having between about 10 to about 30 nucleic acids in length.

8. A method of delivering one or more nucleic acids into a cell comprising contacting the cell with a complex of the one or more nucleic acids and a structure formed from the assembly of one or more compounds in aqueous media having the formula

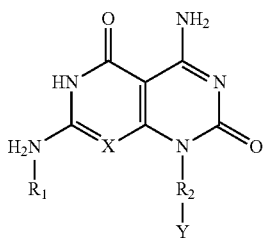

wherein X is CH or nitrogen; $R_2$ is hydrogen or a linker group; Y is absent when $R_2$ is hydrogen or is an amino acid or polypeptide having an amino group covalently bound to an α-carbon of the amino acid and the amino group is covalently bound to the linker group $R_2$; and $R_1$ is hydrogen or an aliphatic moiety; and salts thereof in a manner to deliver the complex into the cell, wherein the cell includes an animal, plant or bacterial cell.

9. The method of claim 1 wherein the linker group is $(CH_2)_n$ where n is an integer of 1, 2, 3, or 4, $(CH_2)_3CO$,

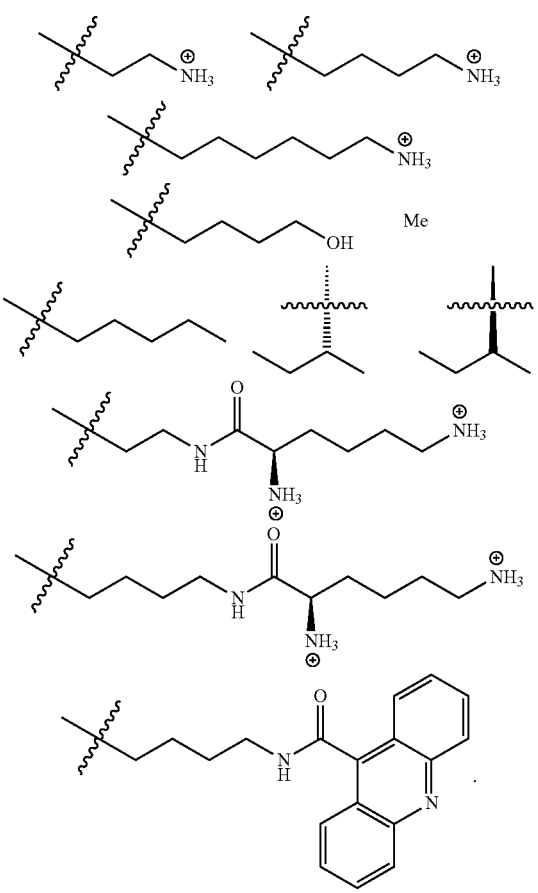

10. The complex of claim 2 wherein the linker group is $(CH_2)_n$ where n is an integer of 1, 2, 3, or 4, $(CH_2)_3CO$,

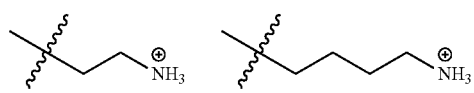

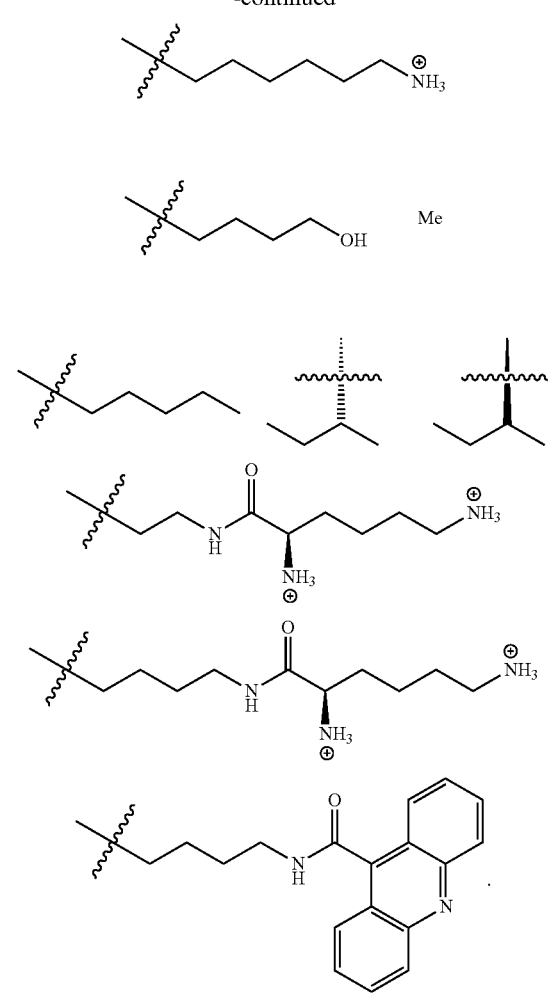

11. A method of making a complex comprising mixing together one or more compounds having the formula

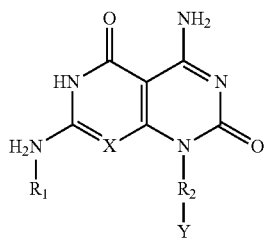

wherein X is CH or nitrogen; $R_2$ is hydrogen or a linker group; Y is absent when $R_2$ is hydrogen or is an amino acid or polypeptide having an amino group covalently bound to an α-carbon of the amino acid and the amino group is covalently bound to the linker group $R_2$; and $R_1$ is hydrogen or an aliphatic moiety; and salts thereof and one or more nucleic acids in aqueous media to form a stable complex of the one or more compounds and the one or more nucleic acids in aqueous media.

12. A method of making a complex comprising mixing together one or more compounds having the formula

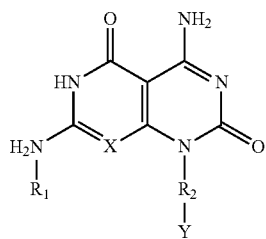

wherein X is CH or nitrogen; $R_2$ is hydrogen or a linker group; Y is absent when $R_2$ is hydrogen or is an amino acid or polypeptide having an amino group covalently bound to an α-carbon of the amino acid and the amino group is covalently bound to the linker group $R_2$; and $R_1$ is hydrogen or an aliphatic moiety; and salts thereof and one or more nucleic acids in aqueous media to form a stable complex of the one or more compounds and the one or more nucleic acids in aqueous media, wherein the linker group is $(CH_2)_n$, where n is an integer of 1, 2, 3, or 4, $(CH_2)_3CO$,

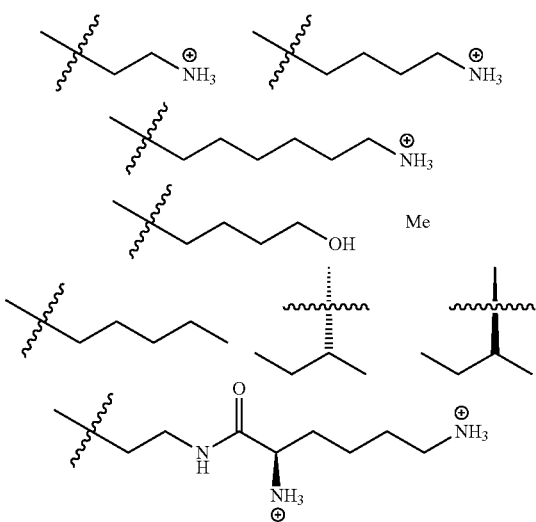

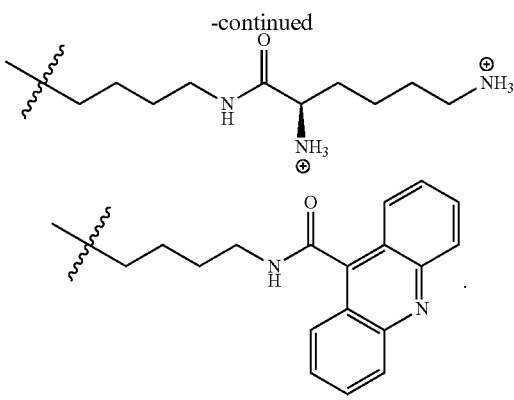

13. A method of making a complex comprising mixing together one or more compounds having the formula

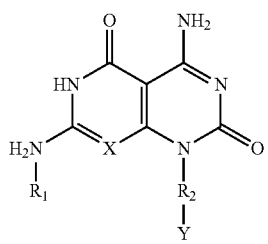

wherein X is CH or nitrogen; $R_2$ is hydrogen or a linker group; Y is absent when $R_2$ is hydrogen or is an amino acid or polypeptide having an amino group covalently bound to an α-carbon of the amino acid and the amino group is covalently bound to the linker group $R_2$; and $R_1$ is hydrogen or an aliphatic moiety; and salts thereof and one or more nucleic acids in aqueous media to form a stable complex of the one or more compounds and the one or more nucleic acids in aqueous media, wherein the mixture is sonicated to form the stable complex in aqueous media.

14. The method of claim 11 wherein the mixture is sonicated and heated to boiling to form the stable complex in aqueous media.

\* \* \* \* \*

UNITED STATES PATENT AND TRADEMARK OFFICE
CERTIFICATE OF CORRECTION

PATENT NO. : 10,344,300 B2
APPLICATION NO. : 14/662334
DATED : July 9, 2019
INVENTOR(S) : Chen et al.

Page 1 of 1

It is certified that error appears in the above-identified patent and that said Letters Patent is hereby corrected as shown below:

On the Title Page

(72) Inventors:
Please delete "Yunpeng Chen" and insert --Yupeng Chen--

In the Specification

Under STATEMENT OF GOVERNMENT INTERESTS Column 1, Line 17:
Please delete "This invention was made with government support under National Institutes of Health number P20 RR024484 and R21 AG027521. The government has certain rights in the invention." and insert --This invention was made with government support under grant numbers P20 RR024484 and R21 AG027521 awarded by the National Institutes of Health. The government has certain rights in the invention.--

Signed and Sealed this
First Day of June, 2021

Drew Hirshfeld
*Performing the Functions and Duties of the
Under Secretary of Commerce for Intellectual Property and
Director of the United States Patent and Trademark Office*